United States Patent
Olefsky et al.

(10) Patent No.: US 9,764,001 B2
(45) Date of Patent: Sep. 19, 2017

(54) TARGET FOR DIAGNOSIS AND TREATMENT OF DIABETES AND CARDIOVASCULAR DISEASES

(71) Applicant: The Regents of the University of California, Oakland, CA (US)

(72) Inventors: Jerrold M. Olefsky, Solana Beach, CA (US); Yun Sok Lee, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/948,539

(22) Filed: Nov. 23, 2015

(65) Prior Publication Data

US 2016/0074478 A1    Mar. 17, 2016

Related U.S. Application Data

(60) Division of application No. 14/451,473, filed on Aug. 5, 2014, now abandoned, and a continuation of application No. PCT/US2013/027860, filed on Feb. 27, 2013.

(60) Provisional application No. 61/605,444, filed on Mar. 1, 2012.

(51) Int. Cl.
  *G01N 33/68*    (2006.01)
  *G01N 33/50*    (2006.01)
  *A61K 38/19*    (2006.01)

(52) U.S. Cl.
  CPC ....... *A61K 38/195* (2013.01); *G01N 33/5091* (2013.01); *G01N 33/6893* (2013.01); *G01N 2333/46* (2013.01); *G01N 2333/4719* (2013.01); *G01N 2333/52* (2013.01); *G01N 2800/042* (2013.01); *G01N 2800/32* (2013.01)

(58) Field of Classification Search
  None
  See application file for complete search history.

(56) References Cited

U.S. PATENT DOCUMENTS

| | | |
|---|---|---|
| 5,712,159 A | 1/1998 | Laurance et al. |
| 7,390,490 B1 | 6/2008 | Imai et al. |
| 2006/0160076 A1 | 7/2006 | Moodie et al. |
| 2012/0040858 A1 | 2/2012 | Ford et al. |

FOREIGN PATENT DOCUMENTS

WO    2005/103684 A2    11/2005

OTHER PUBLICATIONS

PCT International Search Report for PCT Application No. PCT/US2013/027860 mailed Jun. 12, 2013.
Shah et al., "Fractalkine is a Novel Human Adipochemokine Associated with Type 2 Diabetes," Diabetes, 2011, 60:1512-1518.
Wan et al., "Rosiglitazone Activation of PPARγ Suppresses Fractalkine," Journal of Molecular Endocrinology, 2010, 44:135-142.
European Supplementary Search Report for EP Application No. 13 75 5773 mailed Jun. 25, 2015 (8 pages).
Moatti et al., "Polymorphism in the Fractalkine Receptor CX3CR1 as a Genetic Risk Factor for Coronary Artery Disease," Blood, 2001, 97(7):1925-1928.
Wong et al., "Characterization of Fractalkine (CX3CL1) and CX3CR1 in Human Coronary Arteries with Native Atherosclerosis, Diabetes Mellitus, and Transplant Vascular Disease," Cardiovascular Pathology, 2002, 11:332-338.
Medline Plus, obesity, available at http://www.nlm.nih.gov/medlineplus/obesity.html—(referenced Aug. 22, 2013).
St. John Providence Health Center; Preventing Obesity; http://www.stjohnprovidence.org/Health I nfoLib/swarticle.aspx?type=85&id=P07863 (referenced Aug. 22, 2013).
eMedicine Health, diabetes causes, http://www.onhealth.com/diabetes_health/page3.htm#diabetes_causes (referenced Aug. 22, 2013).
United Healthcare, diabetes,X http://www.uhc.com/source4women/health_topics/diabetesirelatedinformation/dOf0417b073bf11 OVgnVCM1 000002f1 Ob1 Oa_htm—referenced Aug. 22, 2013.
WHO Cardiovascular guidelines "Prevention of Cardiovascular Disease: Guidelines for assessment and management of cardiovascular risk" accessed at Mar. 16, 2015 at URL who.inticardiovascular_diseases/guidelines/Full%20text.pdf.
Lesnik, et al. "Decreased atherosclerosis in CX3CR1-/- mice reveals a role for fractalkine in atherogenesis," J. Clin. Invest 111:333-340 (2003).

*Primary Examiner* — James H Alstrum Acevedo
*Assistant Examiner* — Kristina M Hellman
(74) *Attorney, Agent, or Firm* — Eversheds Sutherland (US) LLP

(57) ABSTRACT

Diagnostic, prognostic, and treatment methods, compositions, and kits for enhancing insulin secretion and beta cell numbers and functions, and controlling glycemia associated with diabetes, obesity, atherosclerosis, stroke, myocardial infarction, and other cardiovascular diseases, by modulating FKN/CX3CR1 expression levels or activities, and its downstream signaling pathways in a subject in need or at risk.

1 Claim, 29 Drawing Sheets

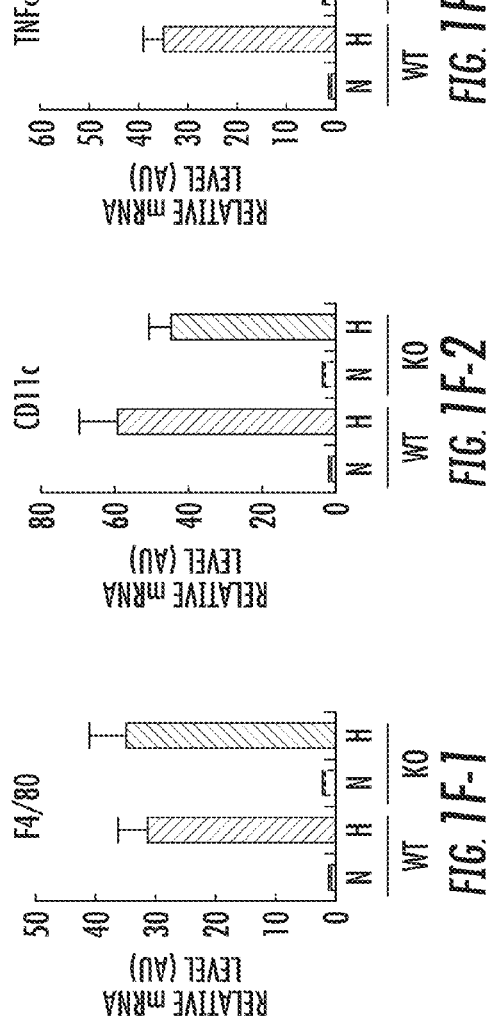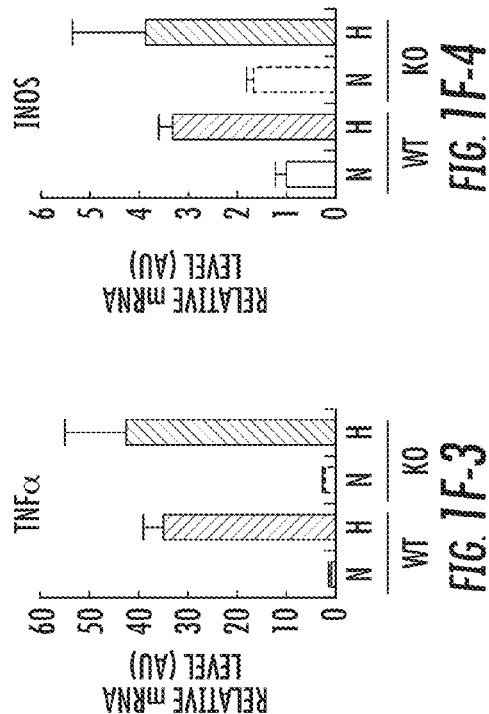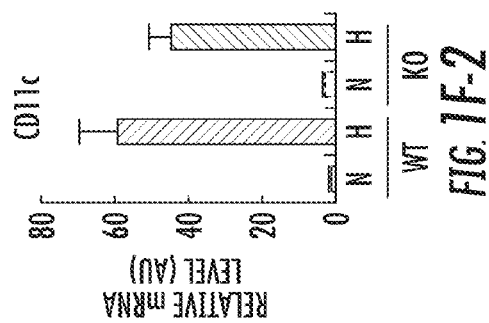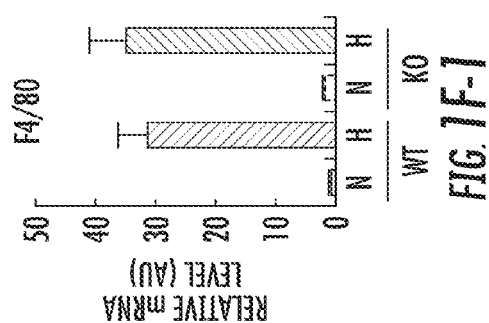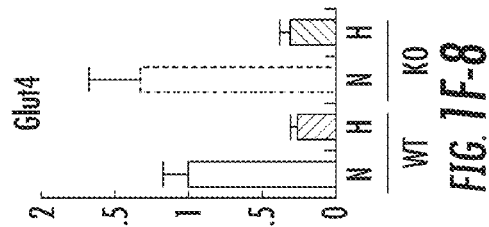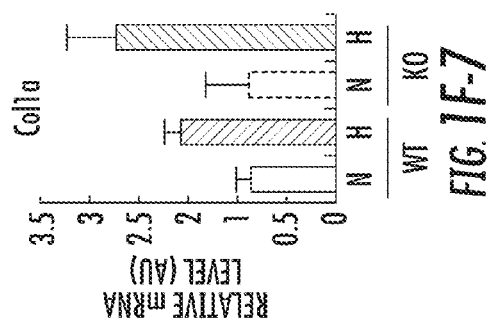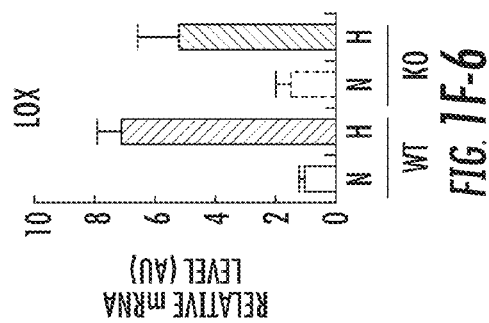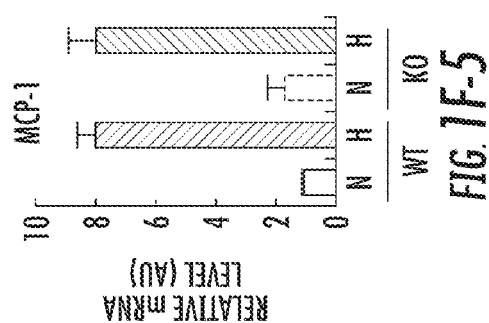

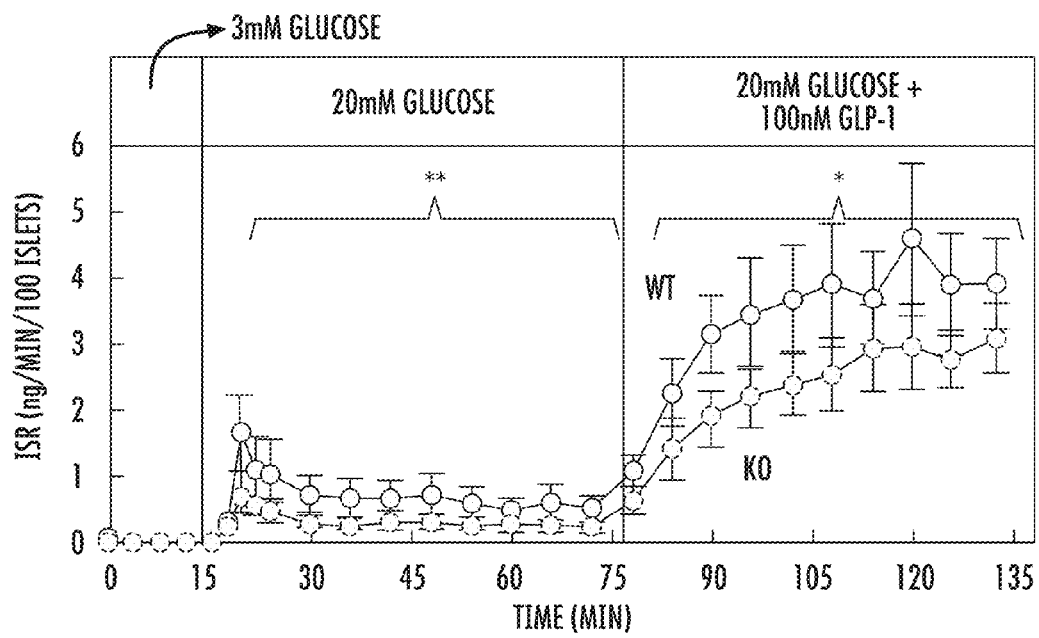
FIG. 3E
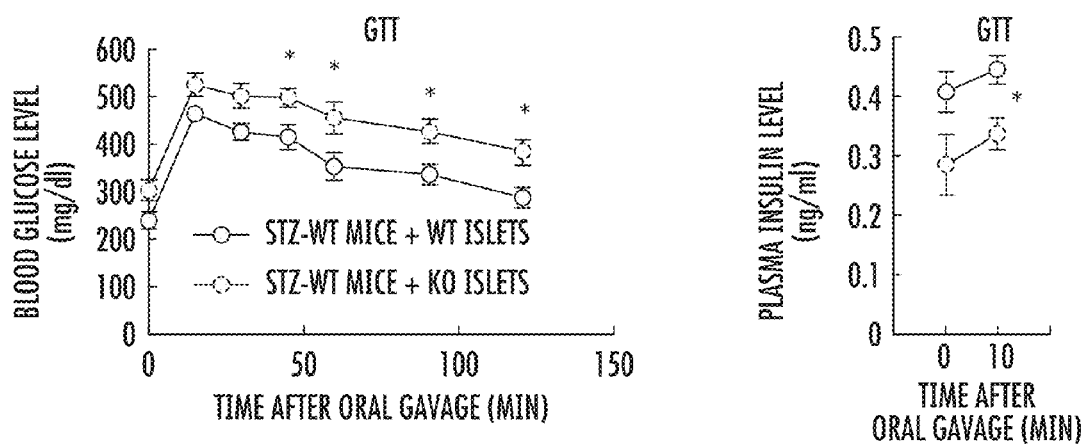
FIG. 3F
FIG. 3G

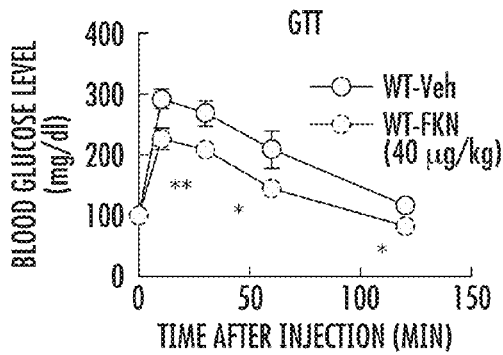
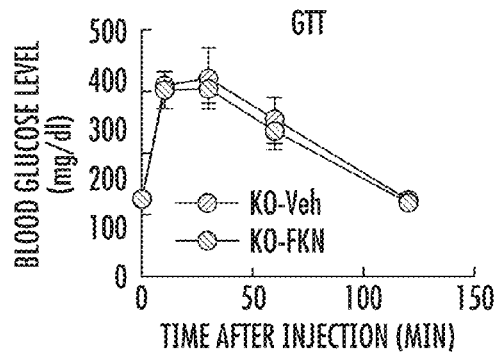
FIG. 5A  FIG. 5B
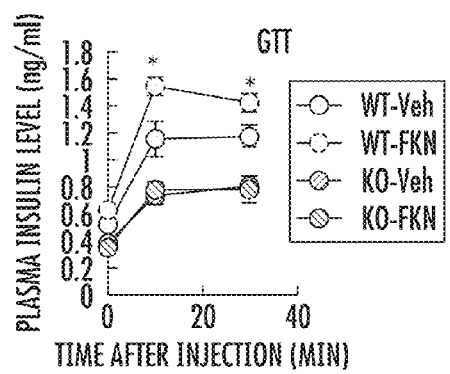
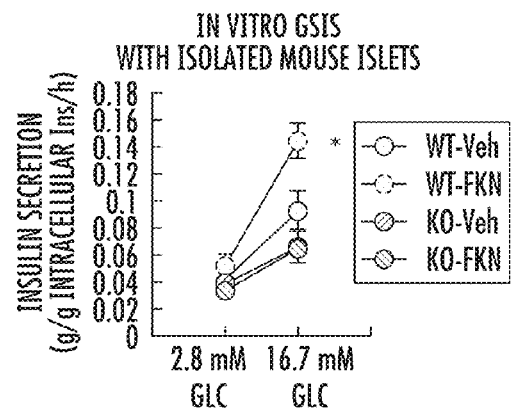
FIG. 5C  FIG. 5D
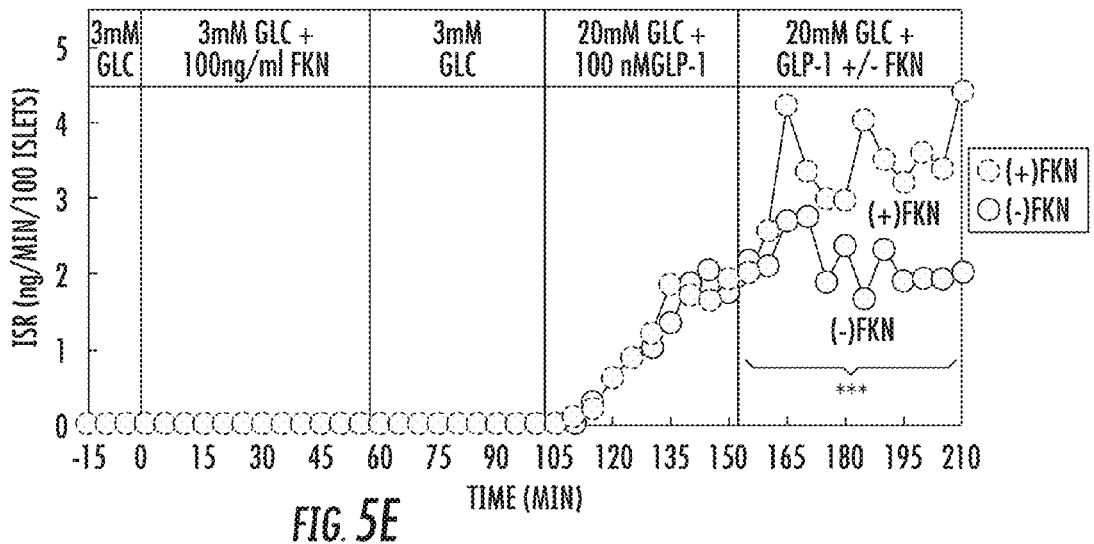
FIG. 5E

TARGET FOR DIAGNOSIS AND TREATMENT OF DIABETES AND CARDIOVASCULAR DISEASES

CROSS REFERENCES TO RELATED APPLICATIONS

This application is a divisional of U.S. application Ser. No. 14/451,473 filed Aug. 5, 2014 which is a continuation of PCT Application No. PCT/US2013/027860 filed Feb. 27, 2013 which claims priority to U.S. Provisional Application Ser. No. 61/605,444 filed on Mar. 1, 2012, the entire contents of which are incorporated by reference herewith.

STATEMENT REGARDING FEDERALLY SPONSORED RESEARCH

This invention was made with Government support under Grant Nos. DK033651, DK063491, and DK074868 awarded by the National Institutes of Health. The Government has certain rights in the invention.

FIELD OF THE INVENTION

The present invention relates to diagnostics and therapeutics for diabetes, atherosclerosis, and other cardiovascular diseases.

BACKGROUND OF THE INVENTION

The prevalence of Type 2 diabetes has risen dramatically in the United States and globally and has now reached epidemic proportions (Olefsky and Glass, 2010). The etiology of this disease involves both insulin resistance and decreased beta cell insulin secretion, and one typically needs both defects (two hit hypothesis) in order to develop the hyperglycemic diabetic state (Defronzo, 2009; Olefsky and Glass, 2010; Weir and Bonner-Weir, 2004). Beta cell failure in type 2 diabetes is associated with at least 2 major mechanisms: reduced overall beta cell mass and decreased insulin secretory function per beta cell (Weir and Bonner-Weir, 2004). In the prediabetic, insulin resistant state, islets respond to the increased insulin demand with enhanced insulin secretion and increased beta cell mass to generate compensatory hyperinsulinemia and maintain relative euglycemia. However, when type 2 diabetes emerges, beta cell function and mass are significantly decreased, with insufficient insulin secretion to compensate for the insulin resistance, resulting in the chronic hyperglycemic diabetic state. This beta cell dysfunction is largely manifested as impaired glucose-stimulated insulin secretion (GSIS) and can be detected in the earliest stages of type 2 diabetes with complete loss of first phase GSIS (Defronzo, 2009; Weir and Bonner-Weir, 2004). On the other hand, decreased beta cell mass is usually not present at the time of diagnosis of type 2 diabetes (Rahier et al., 2008), suggesting that loss of beta cell mass is not responsible for the onset of type 2 diabetes, but rather is a consequence of diabetes.

Recently, it has been proposed that beta cell dysfunction in diabetes is associated with progressive dedifferentiation of beta cells (Jonas et al., 1999; Weir and Bonner-Weir, 2004). This is accompanied by reduced expression of genes necessary for maintaining the mature beta cell phenotype, including PDX-1, Glut2 and insulin, with increased expression of proliferative genes such as c-myc (Jonas et al., 1999; Rahier et al., 2008). This may provide a mechanism for increasing beta cell mass, at the expense of decreased beta cell function.

Fractalkine (also known as CX3CL1 or neurotactin; FKN) is the only member of the CX3C chemokine family, and is expressed in neurons, endothelial cells, hepatocytes and vascular smooth muscle cells (Aoyama et al., 2010; Cardona et al., 2006; Haskell et al., 1999; Lucas et al., 2001; Zernecke et al., 2008). FKN is produced as a membrane-bound protein, and mediates cell-to-cell adhesion and communication by binding to its cognate receptor CX3CR1 (also known as GPR13) (Combadiere et al., 2003; Imai et al., 1997; Lesnik et al., 2003; Tacke et al., 2007; Teupser et al., 2004; Zernecke et al., 2008). In liver, FKN expressed in hepatocyte and stellate cells is anti-fibrotic and can suppress inflammatory activation of Kupffer cells (Aoyama et al., 2010). In the brain, FKN mediates interactions between neurons and glial cells (Cardona et al., 2006). A soluble form of FKN is generated through proteolytic cleavage at the base of the mucin-like stalk, mediated by ADAM 10 and ADAM 17 (Garton et al., 2001; Hundhausen et al., 2003), producing an extracellular form of FKN which can regulate target cells by paracrine mechanisms. Furthermore, soluble FKN can exert paracrine effects in the extracellular space and can also enter the circulation to potentially cause endocrine effects on distant tissues (Shah et al., 2011).

CX3CR1 is the unique receptor for FKN and FKN is the only known ligand for this G protein-coupled receptor (Imai et al., 1997; Zernecke et al., 2008). FKN is expressed as a membrane-bound protein, which can interact with CX3CR1 on adjacent cells to facilitate cell:cell adhesion and communication, and plays a role in the attachment of monocytes/macrophages to CX3CR1 expressing cell types (Haskell et al., 1999; Zernecke et al., 2008).

It has recently been reported that two single nucleotide polymorphisms (T280M and V249I), located in the coding sequence of human CX3CR1, are associated with an increased incidence of type 2 diabetes and metabolic syndrome (Shah et al., 2011; Sirois-Gagnon et al., 2011). These CX3CR1 gene variants result in lower FKN binding affinity, consistent with the view that the FKN/CX3CR1 system plays a beneficial role in the maintenance of proper insulin secretion and glycemic control. On the other hand, circulating levels of soluble FKN are not decreased in type 2 diabetic patients and, in fact, are slightly higher than controls (Shah et al., 2011).

SUMMARY OF THE INVENTION

The present invention provides a novel target and composition and method of diagnosing and prognosing insulin secretion deficiency and/or beta cell dysfunction associated with diabetes. More specifically, the present invention provides that agents modulating CX3CR1 expression and activity, such as soluble FKN protein, or an analogue, or a small molecule which binds to CX3CR1 provide beneficial for improving diabetes by stimulating insulin secretion and improving pancreatic islet function. The invention further provides a novel target and composition and method of diagnosing, prognosing, and preventing glycemia, atherosclerosis, stroke and myocardial infarction by decreasing blood glucose level, or reducing plaqability of macrophages to atherosclerotic lesions, and/or inhibiting apoptosis of vascular smooth muscle cells in necrotic cores of advanced atherosclerotic lesions.

In certain embodiments, the present invention provides that administration of FKN, or an analogue thereof, or a small molecule CX3CR1 agonist improves diabetes by enhancing insulin secretion and/or improving pancreatic islet function. Furthermore, the present invention provides that a CX3CR1 activator increases insulin expression and secretion in pancreatic beta cells by enhancing CX3CR1 downstream signaling pathways including increase of intracellular calcium ion level, as well as regulation of macrophage trafficking and inflammation in pancreas.

In other embodiments, the present invention provides that infusion of the soluble form of FKN, or an analogue, is beneficial for blunting plaque formation by competing with the endogenous membrane-bound FKN expressed on the activated endothelial cells, and inhibiting recruitment and adhesion of monocytes/macrophages.

Thus, the present invention also provides a novel research tool for drug discovery to enhance insulin secretion and control glycemia in patients with diabetes, obesity, atherosclerosis, and cardiovascular diseases, and the development of endogenous or small molecule ligands or therapeutic agents targeting FKN/CX3CR1 for treating diabetes, obesity, atherosclerosis, and other cardiovascular diseases.

BRIEF DESCRIPTION OF THE DRAWINGS

FIGS. 1A to 1F-8. CX3CR1 KO mice exhibit normal body weight, food intake, fat and liver mass, and inflammatory and metabolic gene expression in adipose tissue. (FIG. 1A) Body weight change on HFD. Mean+/−SEM, n=20 for both WT and KO. (FIG. 1B) Cumulative food intake on HFD. Food intake was measured from 5 different cages per group, and 4 mice were housed in each cage. Mean+/−SEM. (FIG. 1C) Liver mass. Mean+/−SEM, n=8 per group. N.S., not significant. NCD, normal chow diet. (FIG. 1D) Epididymal fat mass. Mean+/−SEM, n=8 per group. *, P<0.05. (FIGS. 1E-1 to 1E-2) Immunohistochemistry analysis of epididymal adipose tissue using anti-F4/80 antibody. Representative figures were presented from the analyses of 5 different mice per group. (FIGS. 1F-1 to 1F-8) mRNA expression of inflammatory and metabolic genes in epididymal adipose tissue on NCD and HFD. Mean+/−SEM, n=5 per group. N, normal chow diet; H, high fat diet. AU, arbitrary unit.

FIGS. 2A-1 to 2H-2. CX3CR1 KO mice exhibit impaired glucose tolerance due to reduced insulin secretion. (FIGS. 2A-1 to 2D-3) CX3CR1 KO mice manifest impaired glucose tolerance with normal insulin sensitivity either on NCD (n=11) or HFD (n=12). Mean+/−SEM. (FIGS. 2A-1 to 2A-2) Oral glucose tolerance test. ##, P<0.01 WT-NCD vs KO-NCD; ###, P<0.001 WT-NCD vs KO-NCD; ***, P<0.001 WT-HFD vs KO-HFD. AUC, area under the curve. (FIGS. 2B-1 to 2B-2) Insulin tolerance test. *, P<0.05 WT-HFD vs KO-HFD; **, P<0.01 WT-HFD vs KO-HFD; N.S., not significant. (FIGS. 2C-1 to 2C-3) Plasma insulin (FIGS. 2C-1), C-Peptide (FIGS. 2C-2), and GLP1 (FIGS. 2C-3) levels of NCD mice during OGTT in FIGS. 2A-1 to 2A-2. #, P<0.05; ##, P<0.01. (FIGS. 2D-1 to 2D-3) Plasma insulin, C-peptide, and GLP1 levels of HFD mice during OGTT in FIGS. 2A-1 to 2A-2. *, P<0.05; **, P<0.01. (FIGS. 2E-1 to 2E-2) Intravenous glucose tolerance test (FIGS. 2E-1) and plasma insulin level during IVGTT (FIGS. 2E-2). Mean+/−SEM, n=4 per group. (FIGS. 2F-1 to 2G-2) Plasma insulin and C-Peptide levels of NCD (FIGS. 2F-1 to 2F-2) or HFD (FIGS. 2G-1 to 2G-2) mice during arginine tolerance test. Mean+/−SEM, n=8 per group. #, P<0.05; ##, P<0.01; *, P<0.05; **, 0.01. (FIGS. 2H-1 to 2H-2) Fractalkine neutralization reduces insulin secretion and causes glucose intolerance in WT mice. FKN neutralizing antibody was injected IP to WT mice, and 30 min later the mice were given oral gavage of glucose (2 g/kg) for GTT. Mean+/−SEM, n=10 per group. FIG. 2H-1, plasma insulin level during GTT; FIG. 2H-2, GTT. See also FIG. 8.

FIGS. 3A to 3H-6. CX3CR1 KO islets display reduced insulin secretion with lower expression of genes involved in beta cell function and communication. (FIG. 3A) Static GSIS test using primary mouse islets from WT and CX3CR1 KO mice fed NCD. Mean+/−SEM, n=6 per group. *, P<0.05. (FIG. 3B) Static GSIS test using primary mouse islets from WT and CX3CR1 KO mice fed HFD for 10 weeks. Mean+/−SEM, n=6 per group. (FIG. 3C) Static GSIS in the presence or absence of arginine (Arg; 10 mM) using primary mouse islets. (FIGS. 3D-1 to 3D-2) Knockdown of CX3CR1 decreases GSIS in Min6 cells. Min6 cells were transfected with scrambled siRNA (Scrb) or 2 different CX3CR1 siRNAs (CX-1 and CX-2). 48 h after transfection, GSIS was measured in the presence or absence of 100 ng/ml FKN (FIG. 3D-1), or quantitative realtime RT-PCR was performed for CX3CR1 expression (FIG. 3D-2). , P<0.01; *, P<0.001. (FIG. 3E) Perifusion experiment using islets from WT and CX3CR1 KO mice on NCD. Mean+/−SEM, n=5 per group. *, P<0.05; **, P<0.01. (FIGS. 3F to 3G) STZ-treated mice transplanted with CX3CR1 KO islets are more glucose intolerant than mice transplanted with WT islets. Plasma glucose (FIG. 3F) and insulin (FIG. 3G) levels during GTTs. Mean+/−SEM, n=6 per group. n=5 per group. (FIGS. 3H-1 to 3H-6) mRNA level of genes involved in beta cell function and communication in islets from WT or CX3CR1 KO mice either on chow and HFD. mRNA level of each gene was normalized to 18S rRNA level in the same sample. Mean+/−SEM, n=6 per group. *, P<0.05 WT-NCD vs KO-NCD or WT-NCT vs WT-HFD; **, P<0.01 WT-NCD vs KO-NCD or WT-NCT vs WT-HFD; #, P<0.05 WT-HFD vs KO-HFD. See also FIGS. 9A, 9B, 9C, and 10.

FIGS. 4A to 4I. CX3CR1 KO mice exhibit increased beta cell mass and insulin content. (FIG. 4A) Immunohistochemistry analysis of WT and CX3CR1 KO islets using anti-insulin (green grey-scales) and anti-glucagon (red grey-scales) antibodies. (FIG. 4B) Beta cell mass of WT and CX3CR1 KO mice on NCD. Mean+/−SEM, n=8 per group. *, P<0.05. (FIG. 4C) Pancreatic insulin content. Mean+/−SEM, n=10 per group. (FIG. 4D) Relative islet cell size of WT and CX3CR1 KO mice. Relative islet cell size was calculated by dividing beta cell area by nuclei number. AU, arbitrary unit. Mean+/−SEM, n=8 per group. (FIGS. 4E to 4F-4) Ultramicroscopic analysis of WT and CX3CR1 KO beta cells. (FIG. 4E) Ultramicroscopic pictures of WT and CX3CR1 KO mouse islets on NCD. (FIGS. 4F-1 to 4F-4) Mitochondrial length (FIG. 4F-1) and width (FIG. 4F-2), mitochondrial number per given area (FIG. 4F-3), and cristae abundance (FIG. 4F-4) was calculated using ImageJ software. Mean+/−SEM. 10 different EM pictures of WT and KO islets, and at least 2 mitochondria located nearest to the center of each EM picture were analyzed for the morphometry. AU, arbitrary unit; N.S., not significant. (FIGS. 4G-1 to 4G-2) Vascular density in the islets of WT and CX3CR1 KO mice on NCD was analyzed by immunohistochemistry. Pancreatic sections were co-stained with anti-CD34 (endothelial cell; green grey-scales) and anti-insulin (beta cell; red grey-scales) antibodies, and the intensity of CD34-positive signals in the insulin-positive area was measured and graphed in FIG. 4G-2. Mean+/−SEM, n=6 (WT) and 8 (KO). (FIG. 4H) Immunohistochemistry analysis of mouse islets using anti-CX3CR1 (red grey-scales, on the left), anti-FKN (red grey-scales, on the right), or anti-insulin (green grey-scales) antibodies. (FIG. 4I) Immunohistochemistry of human islet using anti-CX3CR1 (green grey-scales) and anti-insulin (red grey-scales), or anti-glucagon (red grey-scales) antibodies. See also FIGS. 11A, 11B, 11C, and 12.

FIGS. 5A to 5G. FKN enhances insulin secretion and improves glucose tolerance in mice in a CX3CR1-dependent manner. (FIGS. 5A to 5C) WT and CX3CR1 KO mice (on NCD) were injected IP with glucose (2 g/kg)+FKN (40 µg/kg) or glucose+vehicle solution, and blood glucose and insulin levels were measured at the indicated time points. Mean+/−SEM, n=6 (vehicle) or 7 (FKN). (FIG. 5A) Glucose tolerance test in WT mice. *, P<0.05; , P<0.01. (FIG. 5B) Glucose tolerance test in CX3CR1 KO mice. (FIG. 5C) Plasma insulin level during the GTTs. (FIG. 5D) In vitro static GSIS studies using WT and KO islets in the presence or absence of mouse FKN (100 ng/ml). n=6 per group. (FIG. 5E) Perifusion experiment using primary mouse islets in response to the indicated levels of glucose, GLP1 (100 nM) and FKN (100 ng/ml). *, P<0.001. (FIG. 5F) Oxygen consumption rate in islets during the perifusion experiment in FIG. 5E. (FIG. 5G) In vitro static GSIS studies using human islets in the presence or absence of human FKN (100 or 400 ng/ml). n=4. #, P=0.076; *, P<0.05 compared with lane 2. See also FIG. 13.

FIGS. 6A-1 to 6Q-4. FKN stimulates insulin secretion by increasing intracellular calcium levels in a CX3CR1- and MEK-dependent manner. (FIGS. 6A-1 to 6A-4) GSIS test using primary mouse islets with or without pertussis toxin (PTX; 250 ng/ml), Wortmannin (Wort; 10 µM), or PD98059 (50 µM), in the presence or absence of FKN (100 ng/ml). Mean+/−SEM, n=6 per group. FIG. 6D, without glucose), nimodipine (10 µM) (FIG. 6E), control antibody (FIG. 6F), anti-CX3CR1 neutralizing antibody (FIG. 6G), PTX (250 ng/ml) (FIG. 6H), or U0126 (10 µM) (FIG. 6I). Mean+/−SEM. (FIGS. 6L-1 to 6L-4) FKN stimulates expression of genes involved in beta cell function. Primary mouse islets were incubated for 7 days with or without FKN (100 ng/ml), and mRNA expression of PDX-1, NeuroD, Glut2, and HIF-1α was measured by quantitative realtime RT-PCR. Mean+/−SEM. *, P<0.05. (FIGS. 6P-1 to 6P-2) FKN represses binding of ICER-1 to NeuroD promoter. Min6 cells were incubated in serum free media in the presence or absence of palmitate (100 µM) and/or FKN (100 ng/ml). After 48 h, the cells were fixed and subjected to chromatin immunoprecipitation with anti-ICER-1 antibody. (FIGS. 6Q-1 to 6Q-4) Suppressive effect of FKN on ICER-1 expression is abolished by MEK inhibitor (U0126). Min6 cells were incubated with palmitate (Pal; 0.4 mM) in the presence or absence of FKN (100 ng/ml) or U0126 (10 µM). 48 h later, cells were harvested and subjected to quantitative realtime RT-PCR. See also FIGS. 14, 15A-1 to 15C and 16A to 16F.

FIGS. 7A to 7D-2. FKN expression is decreased by aging and HFD in islets. (FIG. 7A) FKN mRNA expression in 7 week old (7 w)-NCD (N), 24 week old (24 w)-NCD, or 24 week old-HFD mice. *, P<0.05 24 w-NCD vs 24 w-HFD. FKN mRNA level was normalized to 18S rRNA level in each sample. Mean+/−SEM, n=6 per group. (FIG. 7B) FKN mRNA expression in 7 week old (7 w)-NCD (N; n=5), 1 year old (1 y)-NCD (n=8), or 1 year old-HFD (H; n=6) mice. Mean+/−SEM. *, P<0.05 7 w-NCD vs 1 y-NCD or 7 w-NCD vs 1 y-HFD. (FIG. 7C) FKN protein expression levels were measured in aliquots of the samples used in FIG. 7B. FKN protein levels were normalized by total protein concentration. Mean+/−SEM. *, P<0.05 7 w-NCD vs 1 y-NCD; **, P<0.01 7 w-NCD vs 1 y-HFD; #, P<0.05 1 y-NCD vs 1 y-HFD. (FIG. 7D-1 to 7D-2) FKN mRNA expression is decreased in in vitro expanded human beta cells. mRNA levels of FKN and CX3CR1 were analyzed in freshly isolated human islets (Islet) or in vitro expanded islets (Exp) as described in experimental procedures. Mean+/−SEM.

FIG. 8. Insulin to glucose ratio during OGTT in FIGS. 2A-1 to 2A-2. Mean+/−SEM.

(FIG. 9A) Oxygen consumption rate change (ΔOCR) of perifused WT islets in response to mitochondrial fuel KIC (10 mM), high glucose (20 mM), or high glucose (20 mM)+nimodipine (5 µM). Mean+/−SEM. (FIG. 9B) Oxygen consumption rate of perifuse CX3CR1 KO islets in response to mitochondrial fuel KIC (10 mM), high glucose (20 mM), or high glucose (20 mM)+nimodipine (5 µM). Mean+/−SEM. (FIG. 9C) Area under the curve in FIGS. 9A and 9B, and statistical analysis.

(FIGS. 11A to 11B) Pancreas mass of WT and CX3CR1 KO mice on either NCD (FIG. 11A) or HFD (FIG. 11B). Mean+/−SEM. (FIG. 11C) Insulin content per islet from WT or CX3CR1 KO mice. For comparison, 20 similar sized islets were handpicked from WT or CX3CR1 KO islets, lysed in acidic ethanol, and subjected to insulin measurement. Insulin content per islet was calculated by dividing total insulin content in the tube by 20. n=6. Mean+/−SEM. *, P<0.05.

FIGS. 15A-1 to 15C. Inhibition of Erk activation by U0126 reduces arginine plus glucose-stimulated intracellular calcium increase and insulin secretion activity in Min6 mouse beta cells (related to FIGS. 6A-1 to 6Q-4). (FIGS. 15A-1 to 15B-3) Intracellular calcium level in Min6 cells. Min6 cells were incubated in 2.8 mM glucose media with or without U0126 (10 µM) for 30 minutes, and then subjected to intracellular calcium measurement in the presence or absence of arginine (10 mM) and/or high glucose (16.7 mM) challenge. (FIGS. 15A-1 to 15A-3) Intracellular calcium level with arginine treatment. (FIGS. 15B-1 to 15B-3) Intracellular calcium level with arginine plus high glucose (16.7 mM) treatment. Area under the curve for first 90 (FIG. 15B-1) or 60 (FIG. 15B-2) seconds was graphed in FIG. 15B-3. (FIG. 15C) Inhibition of Erk activation by U0126 reduces glucose- and arginine plus glucose-stimulated insulin secretion in Min6 cells.

(FIGS. 16A to 16C) Min6 cells were treated with palmitate (Pal; 0.4 mM) in the presence or absence of FKN (100 ng/ml=10.5 nM) or GLP1 (100 nM) for 48 h, followed by caspase-3/7 activity measurement (FIG. 16A), cell viability assays (MTT assay) (FIG. 16B), or cell number counting (FIG. 16C). The fold change in cell number by treatment was measured by dividing total cell number at 48 h after incubation by the number of cells initially plated on each well ($1\times10^4$ cells/well). (FIG. 16D) Ki67 staining of WT and CX3CR1 KO pancreas sections. At age 7 weeks, mice were subjected to chow or 60% HFD for 10 weeks. Total pancreata collected from the mice were fixed with 4% paraformaldehyde, and subjected to IHC. (FIG. 16E) Min6 cells were treated with FKN (100 ng/ml), GLP1 (100 nM), or Wortmannin (Wort; 10 µM), for 15 min, and then subjected to Western blot analysis. (FIG. 16F) FKN suppresses palmitate-induced beta cell apoptosis through a PI3K-dependent pathway. Min6 cells were incubated with palmitate (Pal; 0.4 mM) in the presence or absence of FKN (100 ng/ml) or Wortmannin (Wort; 10 µM) for 48 h, and subjected to caspase-3/7 activity measurement.

DETAILED DESCRIPTION OF THE INVENTION

Figure 1A:
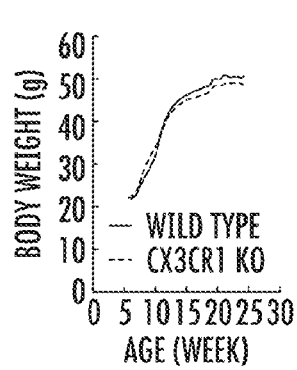

The present invention may be understood more readily by reference to the following detailed description of the preferred embodiments of the invention and the Examples included herein. However, before the present nucleic acids, peptides, compounds, compositions, and methods are disclosed and described, it is to be understood that this invention is not limited to specific nucleic acids, peptides or proteins, compounds, compositions, cell types, host cells, conditions, or methods, etc., as such may, of course, vary, and the numerous modifications and variations therein will be apparent to those skilled in the art. It is also to be understood that the terminology used herein is for the purpose of describing specific embodiments only and is not intended to be limiting. It is also to be understood that as used in the specification and in the claims, "a" or "an" can mean one or more, depending upon the context in which it is used. Thus, for example, reference to "a cell" can mean that at least one cell can be utilized.

The present invention provides a novel diagnostic, prognostic, treatment and research tool methods and compositions for diabetes, obesity, and cardiovascular diseases, including but not limited to, atherosclerosis, stroke and myocardial infarction, by targeting and modulating insulinotropic action of CX3CR1 (aka neuroactin or fractalkine receptor, a CX3C chemokine receptor). In certain embodiments, the treatment method comprises administering to a subject in need a composition comprising a therapeutically effective amount of an agent, such as the soluble endogenous FKN (aka CXCRL1 or fractalkine) ligand, or an analogue thereof, or a CX3CR1 agonist, activator, or antibody that activates CX3CR1 expression and/or activity, thus, enhancing CX3CR1 downstream signaling pathways, such as an increase of intracellular calcium ion level, as well as regulating macrophage trafficking and inflammation in pancreas of the subject.

As used herein, the term "expression level" refers to an amount of DNA, RNA or protein encoded therapy that is expressed in a cell. As used herein, a "gene" includes a DNA polynucleotide containing at least one open reading frame that is capable of encoding a particular polypeptide or protein after being transcribed and translated. Any of the polynucleotide sequences described herein may also be used to identify larger fragments or full-length coding sequences of the gene with which they are associated. Methods of isolating larger fragment sequences are known to those of skill in the art.

As used herein, the terms "polynucleotide," "nucleic acid/nucleotide" and "oligonucleotide" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, DNA, cDNA, genomic DNA, recombinant polynucleotides, branched polynucleotides, plasmids, vectors, isolated DNA of any sequence, isolated RNA of any sequence, nucleic acid probes, and primers. Polynucleotides may be naturally-occurring, synthetic, recombinant or any combination thereof.

As used herein, a "naturally-occurring" polynucleotide molecule includes, for example, a RNA (mRNA) or DNA molecule having a nucleotide sequence that occurs in nature (e.g., encodes a natural protein). As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" also encompasses the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form. The "polynucleotide sequence" is the alphabetical representation of a polynucleotide molecule. A polynucleotide is composed of a specific sequence of four nucleotide bases: adenine (A); cytosine (C); guanine (G); thymine (T); and uracil (U) in place of guanine when the polynucleotide is RNA. This alphabetical representation can be inputted into databases in a computer and used for bioinformatics applications such as, for example, functional genomics and homology searching.

As used herein, the term "protein" or "polypeptide" is interchangeable, and includes a compound of two or more subunit amino acids, amino acid analogs, or peptidomimetics. The subunits may be linked by peptide bonds. In another embodiment, the subunit may be linked by other bonds, e.g., ester, ether, etc. As used herein, the term "amino acid" includes either natural and/or unnatural or synthetic amino acids, including both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

As used herein, the term "therapeutically effective amount" of a therapeutic agent is intended to mean a nontoxic but sufficient amount of such therapeutic agents to provide at least some level of the desired therapeutic effect. The amount that is effective will vary from subject to subject, depending on the age and general condition of the individual, the particular active agent or agents, and the like. Thus, it is not always possible to specify an exact effective amount. However, an appropriate effective amount in any individual case may be determined by one of ordinary skill in the art using routine experimentation.

As used herein, the term "modulating" refers to activating, stimulating, and/or up-regulation. Activator or agonists are compounds that, e.g., bind to, partially or totally stimulate, enhance, increase, activate, sensitize, or up-regulate genes or proteins of CX3CR1 or other molecules in the downstream signaling pathways.

As used herein, the term "therapeutic agents" may refer to any oligonucleotides (antisense oligonucleotide agents), polynucleotides (e.g. therapeutic DNA), ribozymes, dsRNAs, siRNA, RNAi, and/or gene therapy vectors. The term "antisense oligonucleotide agent" refers to short synthetic segments of DNA or RNA, usually referred to as oligonucleotides, which are designed to be complementary to a sequence of a specific mRNA to inhibit the translation of the targeted mRNA by binding to a unique sequence segment on the mRNA. Antisense oligonucleotides are often developed and used in the antisense technology. The term "antisense technology" refers to a drug-discovery and development technique that involves design and use of synthetic oligonucleotides complementary to a target mRNA to inhibit production of specific disease-causing proteins. Antisense technology permits design of drugs, called antisense oligonucleotides, which intervene at the genetic level and inhibit the production of disease-associated proteins. Antisense oligonucleotide agents are developed based on genetic information.

As an alternative to antisense oligonucleotide agents, ribozymes or double stranded RNA (dsRNA), RNA interference (RNAi), and/or small interfering RNA (siRNA), can also be used as therapeutic agents for regulation of gene expression in cells. As used herein, the term "ribozyme" refers to a catalytic RNA-based enzyme with ribonuclease activity that is capable of cleaving a single-stranded nucleic acid, such as an mRNA, to which it has a complementary region. Ribozymes can be used to catalytically cleave target mRNA transcripts to thereby inhibit translation of target mRNA. The term "dsRNA," as used herein, refers to RNA hybrids comprising two strands of RNA. The dsRNAs can be linear or circular in structure. The dsRNA may comprise ribonucleotides, ribonucleotide analogs, such as 2'-O-methyl ribosyl residues, or combinations thereof. The term "RNAi" refers to RNA interference or post-transcriptional gene silencing (PTGS). The term "siRNA" refers to small dsRNA molecules (e.g., 21-23 nucleotides) that are the mediators of the RNAi effects. RNAi is induced by the introduction of long dsRNA (up to 1-2 kb) produced by in vitro transcription, and has been successfully used to reduce gene expression in variety of organisms. In mammalian cells, RNAi uses siRNA (e.g. 22 nucleotides long) to bind to the RNA-induced silencing complex (RISC), which then binds to any matching mRNA sequence to degrade target mRNA, thus, silences the gene.

As used herein, the therapeutic agents may also include any vectors/virus used for gene therapy. The term "gene therapy" refers to a technique for correcting defective genes or inhibiting or enhancing genes responsible for disease development. Such techniques may include inserting a normal gene into a nonspecific location within the genome to replace a nonfunctional gene; swapping an abnormal gene for a normal gene through homologous recombinants, repairing an abnormal gene to resume its normal function through selective reverse mutation; and altering or regulating gene expression and/or functions of a particular gene. As used herein, a term "vector/virus" refers to a carrier molecule that carries and delivers the "normal" therapeutic gene to the patient's target cells. Because viruses have evolved a way of encapsulating and delivering their genes to human cells in a pathogenic manner, most common vectors for gene therapy are viruses that have been genetically altered to carry the normal human DNA. As used herein, the viruses/vectors for gene therapy include retroviruses, adenoviruses, adeno-associated viruses, and herpes simplex viruses. The term "retrovirus" refers to a class of viruses that can create double-stranded DNA copies of their RNA genomes, which can be further integrated into the chromosomes of a host cell, for example, Human immunodeficiency virus (HIV) is a retrovirus. The term "adenovirus" refers to a class of viruses with double-stranded DNA genomes that cause respiratory, intestinal, and eye infections in humans, for instance, the virus that cause the common cold is an adenovirus. The term "adeno-associated virus" refers to a class of small, single-stranded DNA viruses that can insert their genetic material at a specific site on chromosome 19. The term "herpes simplex viruses" refers to a class of double-stranded DNA viruses that infect a particular cell type, neurons. Herpes simplex virus type 1 is a common human pathogen that causes cold sores.

In certain embodiments, the present invention provides a method of treating diabetes, atherosclerosis and other cardiovascular diseases using protein activators, ligands, and/or agonists and their pharmaceutical compositions that directly or indirectly activate CX3CR1 expressions or activity in cells. In certain embodiments, such CX3CR1 selective activators, ligands, agonists comprise any polypeptides, proteins, synthetic, non-toxic, bioactive molecules, and/or immunologically active molecules that are capable of directly or indirectly bind to or interact with CX3CR1, thus, increase insulin expression and secretion in pancreatic beta cells by enhancing CX3CR1 downstream signaling pathways including increase of intracellular calcium ion level, as well as regulate macrophage trafficking and inflammation in pancreas. In other embodiments, such CX3CR1 selective activators, ligands, agonists comprise any polypeptides, proteins, synthetic, non-toxic, bioactive molecules, and/or immunologically active molecules that are capable of directly or indirectly bind to or interact with CX3CR1, thus, decrease blood glucose level or reduce plaqability of macrophages to atherosclerosis lesions, as well as inhibit apoptosis of vascular smooth muscle cells in necrotic cores of advanced atherosclerotic lesions.

In other embodiments, the present invention provides a method of treating diabetes, atherosclerosis and other cardiovascular diseases using any drugs, compounds, small molecules, proteins, antibodies, nucleotides, and pharmaceutical compositions thereof, that are capable of activating CX3CR1 and/or FKN expression levels and/or activities. The present invention contemplates any molecules, known or later developed, that directly or indirectly modulate CX3CR1 or FKN, or its downstream signaling pathways. As used herein, the term "pharmaceutical composition" contemplates compositions comprising one or more therapeutic agents as described above, and one or more pharmaceutically acceptable carriers or vehicles. As used herein, the term "pharmaceutically acceptable carriers or vehicles" comprises any acceptable materials, and/or any one or more additives known in the art. As used herein, the term "carriers" or "vehicle" refer to carrier materials suitable for drug administration through various conventional administration routes known in the art. Carriers and vehicles useful herein include any such materials known in the art, which are nontoxic and do not interact with other components of the composition in a deleterious manner.

The present invention also contemplates any conventional methods for formulation of pharmaceutical compositions as described above. Various additives, known to those skilled in the art, may be included in the formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

The present invention also provides a diagnostic method for diabetes, atherosclerosis, or other cardiovascular diseases by comparing CX3CR1 and/or FKN expression and/or activity levels in subjects at risk for such disorders vs. normal subjects. In certain embodiments of the present invention, both CX3CR1 and/or FKN mRNA and protein expression levels in cells from a subject at risk for these disorders are compared to a baseline level of CX3CR1 and/or FKN mRNA and protein expression levels in normal cells, wherein a decreased level of CX3CR1 and/or FKN mRNA and/or protein expression levels or a reduced CX3CR1 and/or FKN1 activity in relation to the baseline level of CX3CR1 and/or FKN mRNA and/or protein expression or activity levels indicates an association with diabetes, obesity, atherosclerosis, and/or other cardiovascular diseases in that subject. The diagnostic method of the present invention is performed using any biological fluid and/or tissue containing pancreatic cells and/or islets.

The present invention further provides a kit for a diagnosis of diabetes, obesity, atherosclerosis and other cardiovascular diseases comprising biomarker detecting reagents for determining CX3CR1 and/or FKN expression or activity levels, and instructions for their use in diagnosing these disorders. As used herein, the term "biomarker" refers to an indicator and/or prognostic factor of biologic or pathologic processes or pharmacologic responses to a therapeutic intervention. As used herein, the term "prognostic factor" refers to any molecules and/or substances contributing to a predicted and/or expected course of diabetes, obesity, atherosclerosis, and other cardiovascular diseases including various developments, changes and outcomes of the disease. As used herein, the term "detecting reagents" refer to any substances, chemicals, solutions used in chemical reactions and processes that are capable of detecting, measuring, and examining CX3CR1 and/or FKN. In certain embodiments, the biomarker detecting reagents used herein comprise chemicals, substances, and solutions that are suitable for determining either mRNA or protein, or both expression and/or activity levels of CX3CR1 and/or FKN.

One of the detecting reagents may include immunologically active molecules comprising an antibody molecule or a fragment thereof that specifically binds to CX3CR1 or FKN or an antigen for CX3CR1 or FKN. The term "antibody" as used herein encompasses monoclonal antibodies (including full length monoclonal antibodies), polyclonal antibodies, multispecific antibodies (e.g., bispecific antibodies), and antibody fragments so long as they exhibit the desired biological activity of binding to CX3CR1 or FKN. The term "antibody fragments" comprise a portion of a full length antibody, generally the antigen binding or variable region thereof. Examples of antibody fragments include Fab, Fab', F(ab')$_2$, and Fv fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The "monoclonal antibodies" may also be isolated from phage antibody libraries using the techniques known in the art.

The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

The term "single-chain Fv" or "sFv" antibody fragments comprise the VH and VL domains of antibody, wherein these domains are present in a single polypeptide chain. Generally, the Fv polypeptide further comprises a polypeptide linker between the VH and VL domains which enables the sFv to form the desired structure for antigen binding.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-polyacrylamide gel electrophoresis under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

In order to avoid potential immunogenicity of the monoclonal antibodies in human, the monoclonal antibodies that have the desired function are preferably humanized. "Humanized" forms of non-human (e.g., murine) antibodies are chimeric antibodies that contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. Antibodies capable of immunoreacting to particular CX3CR1 or FKN are made using conventional methods known in the art.

Other molecules which selectively bind to CX3CR1 or FKN gene products (e.g. mRNAs) known to those skilled in the art, or discovered in the future are contemplated within the scope of the present invention. Such molecules include primers and/or probes comprising desired DNA, RNA, and/or DNA/RNA hybrid sequences. As used herein, the term "primer" refers to a segment of DNA or RNA that is complementary to a given DNA or RNA sequences (e.g. sequences of a particular CX3CR1 or FKN) and that is needed to initiate replication by DNA polymerase, and a term "probe" refers to a substance, such as DNA, that is radioactively labeled or otherwise marked and used to detect or identify another substance in a sample. As used herein, the term "primer" and "probe" are used interchangeably, and typically comprise a substantially isolated oligonucleotide typically comprising a region of nucleotide sequence that hybridizes under stringent conditions to at least about 12, preferably about 25, more preferably about 40, 50, or 75 consecutive nucleotides of a sense and/or an antisense strands of a nucleotide sequence of CX3CR1 or FKN or naturally occurring mutants thereof.

As used herein, primers based on the nucleotide sequence of CX3CR1 or FKN can be used in PCR reactions to clone homologs of CX3CR1 or FKN. Probes based on the nucleotide sequences of CX3CR1 or FKN can be used to detect transcripts or genomic sequences encoding the same or substantially identical polypeptides or proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express or over-express CX3CR1 or FKN, such as by measuring a level of encoding nucleic acid, in a sample of cells, e.g., detecting mRNA levels or determining whether a genomic gene has been mutated or deleted.

In certain embodiments, the biomarkers and/or prognostic factors for diagnosing and monitoring diabetes, obesity, atherosclerosis or other cardiovascular diseases comprise CX3CR1 or FKN. In yet certain embodiments, the kit of the present invention comprise any detecting reagents that are capable to detect mRNA, protein, or both, expression or activity levels of CX3CR1 or FKN. In yet other embodiments, the kit of the present invention comprise means for calculating the expression or activity levels of CX3CR1 or FKN. The kit of the present invention further comprises an instruction for use in diagnosing and monitoring diabetes, obesity, atherosclerosis or other cardiovascular diseases. In one preferred embodiment, the instruction in the kit provides that a decreased or reduced CX3CR1 or FKN and/or protein expression or activity levels indicates an association with diabetes, obesity, atherosclerosis, or other cardiovascular diseases.

Throughout this application, various publications are referenced. The disclosures of all of these publications and those references cited within those publications in their entireties are hereby incorporated by reference into this application in order to more fully describe the state of the art to which this invention pertains.

Several examples are presented below. It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

The following examples provide a novel regulatory pathway for the FKN/CX3CR1 system in the modulation of beta cell insulin secretory function. It was found that CX3CR1 KO mice develop hyperglycemia with reduced nutrient-stimulated insulin secretion and that isolated islets from KO mice produce less insulin in response to a variety of stimuli compared to WT islets. Furthermore, in vivo FKN administration leads to increased plasma insulin levels with improved glucose tolerance, while in vitro FKN treatment of isolated islets directly enhances beta cell insulin secretion.

Here a novel mechanism for regulating beta cell function through the FKN/CX3CR1 system is described. CX3CR1 KO mice develop glucose intolerance on both chow and HFD due to decreased insulin secretion. Neutralization of circulating FKN by in vivo administration of anti-FKN antibodies recapitulated this effect, causing glucose intolerance with diminished insulin secretion, demonstrating that FKN is necessary for ongoing maintenance of circulating insulin levels. The impaired insulin secretion represents a primary beta cell defect, since isolated islets from CX3CR1 KO mice exhibited impaired GSIS compared to WT islets and CX3CR1 KO islets transplanted into STZ-induced diabetic mice had an attenuated ability to correct the diabetic state compared to transplantation of WT islets. Finally, in vivo administration of FKN treatment led to improved glucose tolerance with increased insulin secretion and in vitro treatment directly caused increased GSIS in isolated mouse and human islets. In contrast, FKN was without effect on insulin secretion in CX3CR1 KO mice or in islets from KO animals. Taken together, these studies reveal a novel regulatory system for beta cell insulin secretion, suggesting that a FKN-based biotherapeutic, or a small molecule CX3CR1 agonist, could be a useful therapeutic tool in the treatment of type 2 diabetes.

The in vitro studies demonstrate that FKN is not a direct insulin secretagogue, since it does not enhance insulin secretion in the absence of glucose or at low glucose concentrations. Instead, FKN only exerts its effects by potentiating GSIS, arginine-, or GLP1-mediated insulin secretion. The in vitro studies show that the acute effects of FKN on insulin secretion are not due to changes in mitochondrial function, cyclic AMP levels, or increased PKA activity. In the presence of glucose, FKN causes an increase in intracellular calcium levels through a MEK-dependent mechanism. Combined with the fact that CX3CR1 deletion impairs the insulin secretory response to arginine, this suggests that the effects of FKN on insulin secretion are exerted at a downstream step common to several stimulatory inputs, most likely involving MEK-dependent calcium mobilization events.

These data demonstrate that FKN has acute effects to potentiate GSIS and GLP1-stimulated insulin secretion, but it is also possible that FKN has chronic effects on beta cell function as well. Thus, CX3CR1 KO islets display decreased expression of a set of genes characteristic of normal, fully functioning beta cells, including PDX1, NeuroD, GLUT2, urocortin3, and CX36. Furthermore, chronic FKN treatment of WT islets leads to increased expression of these genes. These observations suggest that CX3CR1 deletion, with ablation of FKN signaling, produces beta cells that are partially dedifferentiated. Indeed, the KO islets are characterized by increased total cell mass due to increased numbers of smaller beta cells, and it has been reported that reduced beta cell size is associated with impaired insulin secretory function (Giordano et al., 1993; Pende et al., 2000). Furthermore, it was found that ICER-1 is induced in CX3CR1 KO islets while FKN treatment of Min6 cells suppresses palmitate-induced ICER-1 expression. ICER-1 is a transcriptional repressor which can inhibit genes associated with the normal differentiated beta cell functional state. It has been shown that ICER-1 is induced by saturated fatty acids, oxidized LDL, hyperglycemia, and high fat diet and ICER-1 induction can cause beta cell dysfunction by inhibiting expression of CX36, as well as components of the insulin secretory machinery as exemplified in FIGS. 3A to 3H-6 (Favre et al., 2011; Hussain et al., 2000; Zhou et al., 2003). This suggests that increased ICER-1 expression in CX3CR1 KO beta cells is mechanistically linked to a more chronic state of beta cell dysfunction. In this context, it is important to note that in vitro siRNA-mediated knockdown of CX3CR1 in Min6 cells caused decreased GSIS, suggesting that the in vivo decrease in insulin secretion in the KO mice was not due to an in vivo beta cell developmental defect.

Together, these studies describe a novel pathway regulating beta cell secretory function in which FKN stimulates CX3CR1 to promote increased insulin secretory responses. CX3CR1 deficiency mimics some of the beta cell abnormalities observed in diabetic islets and FKN treatment restores these defects towards normal. In mice, aging and the HFD/obese hyperglycemic state are associated with decreased islet FKN expression. Thus, attenuation of this newly identified FKN/CX3CR1 system could underlie some of the defects in diabetic islets. Furthermore, a FKN-based biotherapeutic, or a small molecule CX3CR1 agonist, could have utility in the treatment of type 2 diabetes.

Example 1

Experimental Procedures

Animals and Treatments 7 week old male C57BL/6N and CX3CR1 knockout mice were purchased from Taconic (USA). GTT and ITT results from the CX3CR1 KO mice were confirmed in CX3CR1$^{gfp/gfp}$ knockin mice obtained from Jackson Laboratory (USA). All the mice were housed in colony cages in 12 h light/12 h dark cycles. For HFD study, 8 week old mice were subjected to NCD or 60% HFD (Research Diets, Inc; USA). For oral glucose tolerance test, the mice were fasted for 6 h and basal blood samples were taken, followed by oral gavage of 2 g/kg bolus glucose. Blood samples were drawn at 10, 20, 30, 45, 60, 90 and 120 min after oral gavage. For intravenial glucose tolerance test, the mice were surgerized for catheter implantation to jugular vein as described previously (Lee et al., 2011). After 3 days of recovery, the mice were fasted for 5 h, and then transferred to restrainers. After 1.5 h of stabilization, blood samples were drawn from tail for basal glucose and insulin measurement, followed by 1 g/kg bolus glucose injection through the jugular catheter. Blood samples were drawn for glucose and/or insulin measurement at 1, 5, 10, 30 and 60 min after glucose injection. For insulin tolerance test, mice were fasted for 6 h, and basal blood samples were taken, followed by intraperitoneal injection of insulin (0.4 U/kg for NCD mice, 0.6 U/kg for HFD mice). For FKN neutralization experiment, mice were IP injected with anti-FKN neutralizing antibody (2 μg/mouse; Torrey Pines Biolabs, USA). For arginine tolerance test, the mice were fasted for 6 h and basal blood samples were taken, followed by IP injection of 1 g/kg arginine. All animal procedures were in accordance with the research guidelines for the use of laboratory animals of University of California, San Diego.

Plasma Protein Measurements

Plasma insulin (ALPCO, USA), C-peptide (ALPCO, USA), GLP1 (active 7-36 GLP1; Millipore, USA), and fractalkine (R&D systems, USA) levels were measured by ELISA.

Islet Isolation and Transplantation

For primary mouse islet isolation, the bile duct near ampullar vater was ligated, and the common bile duct was cannulated and injected with 3 ml of KRB buffer containing collagenase XI (800 U/ml; Sigma, USA). The pancreas was dissected from the surrounding tissues, removed, and incubated in a stationary bath for 13 min at 37 C. The digested tissue was washed with KRB without collagenase, and then the islets were purified by a density gradient (Histopaque 1077 and 1119; Sigma) centrifuged at 3,000 g for 25 min. A single aliquot of 200 freshly isolated islet equivalents was aspirated into a 200 μl pipette tip, and then the pipette tip was connected to a silicon tube (I.D.×O.D.=0.76 mm×1.67 mm; Dow Corning, USA). Under anesthesia, the left kidney of the recipient mouse was exposed through a lumbar incision. A capsulotomy was performed on the caudal outer surface of the kidney, and tip of the tubing was advanced under the capsule, followed by slow injection of the islets using 20 µl pipette attached to the 200 µl pipette tip. The tube was then removed and the capsulotomy was cauterized with a disposable cautery pen (Aaron medical, USA).

Histology Analyses

To identify FKN and CX3CR1 expression in pancreatic tissues, deparaffinized tissue sections were blocked for endogenous peroxidase and endogenous biotin and overlaid with 0.5% fish gelatin in phosphate-buffered saline Tween 20. Sections were then incubated with control IgG, anti-insulin (N1542; Dako, USA), anti-glucagon (PA1-85465; Pierce, USA), anti-CD34 (MEC17.4; Novus, USA), anti-FKN (TP-233; Toney pines biolabs, USA) or anti-CX3CR1 (ab8021; Abcam, USA) antibodies, followed by incubation with secondary antibodies conjugated with Alexa488 (Jackson Laboratories, USA) or Cy3 (Jackson). For islet morphometric study, specimens were viewed on a Zeiss AxioObserver Z1 microscope, and 24-bit TIFF images were acquired with a Zeiss AxioCam digital camera driven by Zeiss AxioVision 3.1 software (Carl Zeiss, Germany). Images were processed with Adobe Photoshop CS4 (Adobe Systems, USA). Relative pancreatic areas of beta cells were calculated by dividing insulin-positive area by total pancreatic area measured using Image J software (U.S. National Institutes of Health, USA).

Measurement of Insulin Secretory Response from Isolated Islets

Isolated mouse islets were cultured overnight in mouse islet media (DMEM containing 1 g/L glucose, 10% v/v FBS, 0.1% v/v Penicillin/Streptomycin). Islets of similar sizes were harvested by hand-picking manually under a microscope. For dynamic resolution of insulin secretory response, islets were perifused at 37° C., 5% CO2 in a system comprised of a pump, gas equilibrating system and islet chamber, which concomitantly measured oxygen consumption rate while collecting outflow fractions for subsequent assay of insulin fraction collector, as described previously (Sweet et al., 2004). The perifusate, Krebs Ringer Bicarbonate buffer (2.6 mmol/l $CaCl_2/2H_2O$, 1.2 mmol/l $MgSO_4/7H_2O$, 1.2 mmol/l $KH_2PO_4$, 4.9 mmol/l KCl, 98.5 mmol/l NaCl, and 25.9 mmol/l $NaHCO_3$ (all from Sigma-Aldrich, St. Louis, Mo.) supplemented with 20 mmol/l HEPES/Na-HEPES (Roche, Indianapolis, Ind.) and 0.1% BSA (Serological, Norcross, Ga.).), was pumped at 100 microL/min when oxygen consumption was measured and 250 microL/min when only insulin secretion was measured (in order to resolve first phase insulin secretory response to glucose). Glucose and GLP1 were added to the buffer as indicated in the figures. Fractions were collected and kept at −80° C. until analysis of insulin. For static GSIS assays with mouse islets, approximately 20 islets were hand picked, incubated for 2 hours in KRB buffer at 37° C., 5% $CO_2$, and then incubated for 75 min with 2.8 mM or 16.7 mM glucose in the same conditions. For static GSIS assays with human islets, overnight shipped cadaveric human islets (Prodo Labs, USA) were washed with recovery media (Prodo Labs, USA) twice, and incubated overnight in the recovery media at 37° C., 5% $CO_2$. Next day, the islets were washed twice with 2.8 mM glucose DMEM, and incubated overnight in 2.8 mM glucose DMEM supplemented by 1% free fatty acid free BSA, at 37° C., 5% $CO_2$. On day 3, the islets were washed with fresh 2.8 mM glucose media, and then incubated for 60 min in 2.8 mM or 16.7 mM glucose media with or without FKN. Insulin concentrations in the supernatant were determined using Ultrasensitive mouse or human Insulin ELISA kits (Alpco).

Intracellular Calcium Level Measurement

The Cytoplasmic free calcium ion concentration in Min6 cells was measured by fura-2 fluorescence ratio digital imaging. Briefly, Min6 cells, grown on coverslips, were loaded with 5 µM fura-2 AM [dissolved in 0.01% Pluronic F-127 plus 0.1% DMSO in KRB] at room temperature for 60 min and then washed in fresh KRB for 30 min. The coverslips with Min6 cells were mounted in a perfusion chamber on a Nikon microscope stage. The ratio of fura-2 fluorescence with excitation at 340 or 380 nm (F340/380) was followed in a single cell over time and captured with an intensified CCD camera (ICCD200) and a MetaFluor Imaging System (Universal Imaging, Downingtown, Pa.). Data from more than 50 cells on each coverslip was analyzed for statistics, and the data was confirmed by at least 3 independent experiments.

cAMP Level Measurement

Intracellular cAMP level of Min6 cells was measured using Bridge-it cAMP assay kit (Mediomics, LLC, USA).

Electron Microscope

Scanning electron micrographs were taken using Phillips 12 XL30 ESEM in an environmental mode at Calit2-Nano3 facility. Five non-overlapping areas in the central region of a single SEM image, each with 7 ommatidia, were selected and used for ommatidial size measurement. For transmission electron micrographs, primary mouse islets were fixed in 2% paraformaldehyde plus 2.5% glutaraldehyde (Ted Pella, Redding, Calif.) in 0.1 M sodium cacodylate (pH 7.4) on ice for 1 hr. The samples were washed three times with buffer consisting of 0.1 M sodium cacodylate plus 3 mM calcium chloride (pH 7.4) on ice and then post-fixed with 1% osmium tetroxide, 0.8% potassium ferrocyanide, 3 mM calcium chloride in 0.1 M sodium cacodylate (pH 7.4) for 1 h, washed three times with ice-cold distilled water, en bloc stained with 2% uranyl acetate at 4° C. for 1 h, dehydrated through graded ethanol solutions, and embedded in Durcupan ACM resin (Fluka, St. Louis, Mo.). Ultrathin (80 nm) sections were post-stained with uranyl acetate and lead salts prior to imaging using a JEOL 1200FX transmission EM operated at 80 kV. The negatives were digitized at 1800 dpi using a Nikon CoolScan system, giving an image size of 4033×6010 pixels and a pixel resolution of 1.77 nm.

Human Islet and In Vitro Beta Cell Expansion

The human islet and beta cell samples were prepared and analyzed as described previously (Kayali et al., 2007). Human adult islets were provided by the Islet Cell Resource Center Basic Science Human Islet Distribution Program, and the Islet Transplant Program at the University of Illinois at Chicago. The islets were from six cadaveric donors aged 25-55 years, and 60-90% pure in mature islets (viability of 80-90%). Islets were expanded by the Whittier or NIH protocols as described previously (Kayali et al., 2007). Briefly, in the Whittier Protocol isolated islets were hand-picked after dithizone staining, partially dissociated, and plated on HTB-9 coated dishes using RPMI-1640 (Mediatech, Herndon. Va.) supplemented with 2 mM L-glutamine and 10% fetal bovine serum and 25 ng/ml hepatocyte growth factor. The cells were passaged 1:2 upon confluence. In the NIH protocol, 2,000 islet equivalents enriched by retention on a 40 µm filter were seeded onto tissue culture-treated dishes in CMRL-1066 medium (Invitrogen, USA) containing 2 mM L-glutamine and 10% fetal bovine serum. Cells were cultured for 2 weeks (passage 0), and after that cells were harvested every 4-7 days with trypsin and subcultured (1:2) for up to 2 months. RNA was isolated from fresh human adult islets or islets cultured in monolayer for three or four passages. Microarray analysis was performed on the RNA samples as described previously (Kayali et al., 2007; Kutlu et al., 2009).

Statistics

The results are shown as means±SEM. All statistical analysis was performed by Student's t test or ANOVA in Excel (Microsoft); P<0.05 was considered significant.

Example 2

Figure 1B:
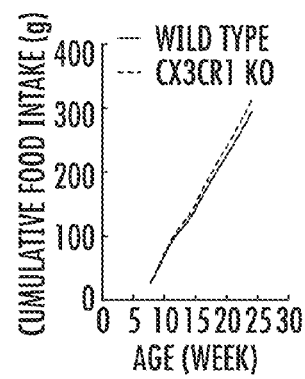
Figure 1C:
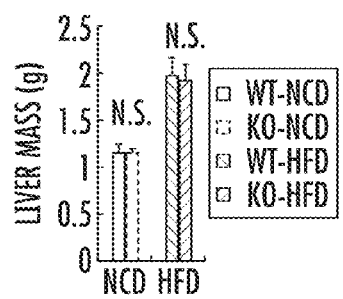
Figure 1D:
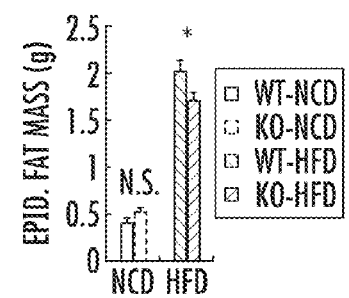

CX3CR1-Deficient Mice Exhibit Impaired Glucose Tolerance with Reduced Insulin Secretion Obesity causes inflammation and insulin resistance and the FKN/CX3CR1 system plays a role in monocyte attachment and immune cell migration (Combadiere et al., 2003; Hotamisligil et al., 1995; Lee et al., 2010; Lee et al., 2011; Lesnik et al., 2003; Olefsky and Glass, 2010; Tacke et al., 2007; Teupser et al., 2004). To address the potential effect of this receptor on obesity-induced inflammation, lean and obese CX3CR1 KO mice were studied. The KO mice exhibited normal food intake, body weight gain, and liver mass either on chow or high fat diet (HFD) (FIGS. 1A-1C). Adipose tissue mass was the same between KO and WT mice on chow diets, but was slightly lower in the KO mice on HFD (FIG. 1D).

Interestingly, it was found no evidence that FKN or CX3CR1 play a role in macrophage accumulation in adipose tissue or liver or in inflammation-induced insulin resistance. For example, macrophage infiltration (FIGS. 1E-1 to 1E-2) and expression of macrophage marker genes, such as F4/80 and CD11c (FIGS. 1F-1 to 1F-8), was not altered in the adipose tissue of KO mice. Moreover, CX3CR1 KO did not affect HFD-induction of genes involved in inflammation (iNOS, MCP-1, and TNF-α) or fibrosis (lysyl oxidase and collagen 1a) in adipose tissue (FIGS. 1F-1 to 1F-8). Consistent with this, Lumeng also recently reported that CX3CR1 deficiency is without effect on adipose tissue macrophage content in HFD mice (Morris et al., 2012). Furthermore, the decrease in GLUT4 expression which typically occurs on HFD was not attenuated by the CX3CR1 KO (FIGS. 1F-1 to 1F-8), suggesting that CX3CR1 KO does not affect insulin resistance.

Figures 1, 1E:
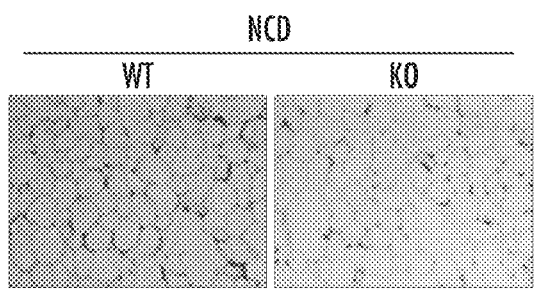
Figures 1, 1E, 2:
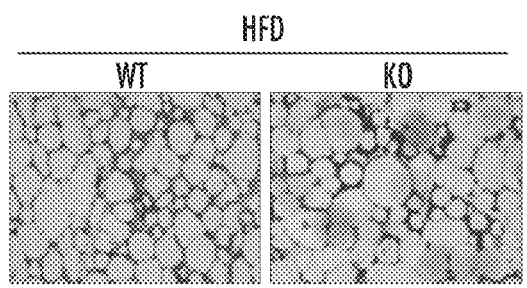
Figures 1, 2A:
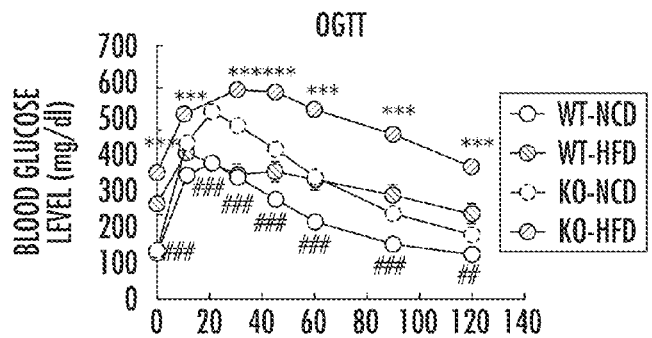
Figures 2, 2A:
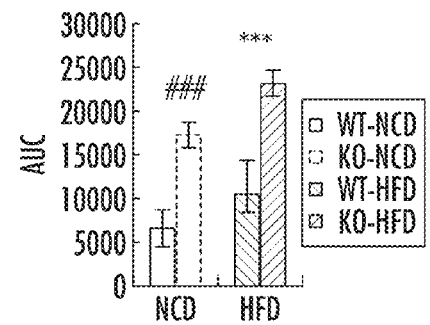
Figures 1, 2B:
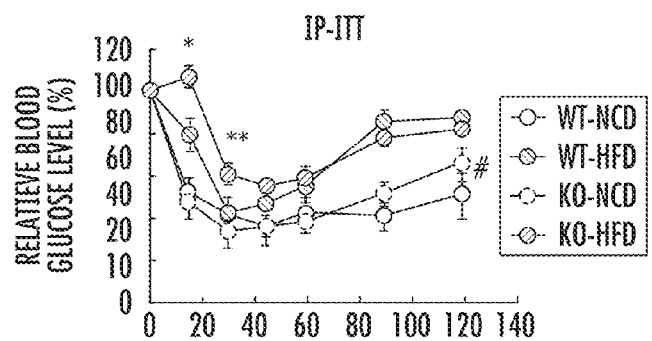
Figures 2, 2B:
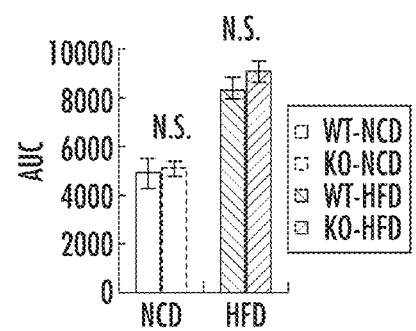
Figures 1, 2C:
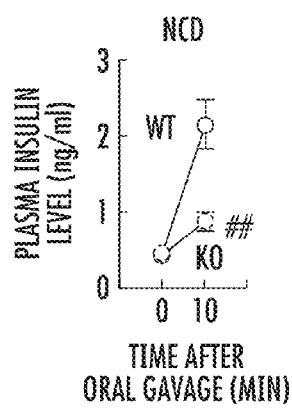
Figures 2, 2C:
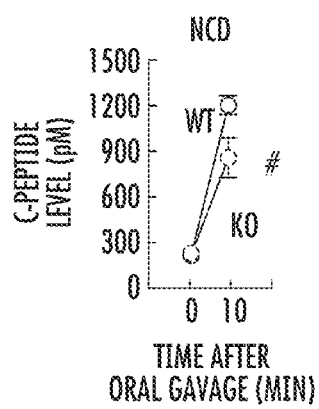
Figures 2, 2C, 3:
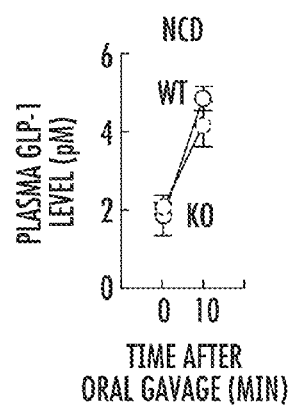
Figures 1, 2D:
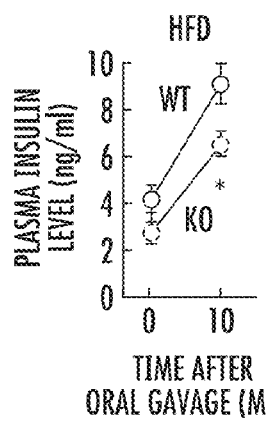
Figures 2, 2D:
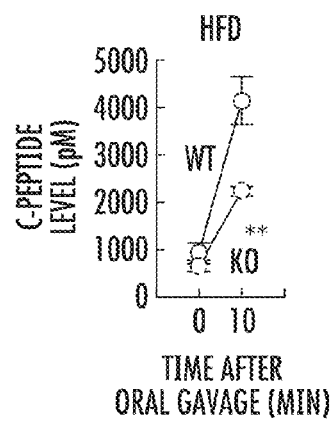
Figures 2, 2D, 3:
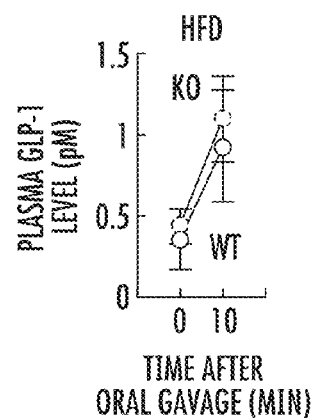
Figures 1, 2E:
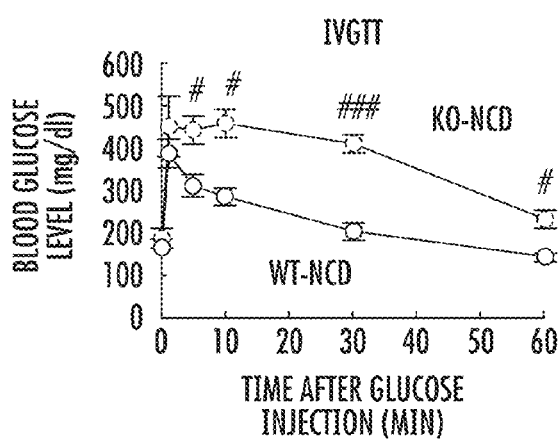
Figures 2, 2E:
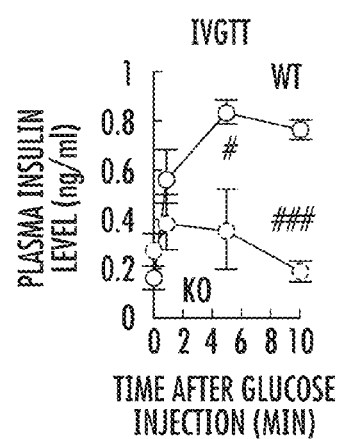
Figures 1, 2F:
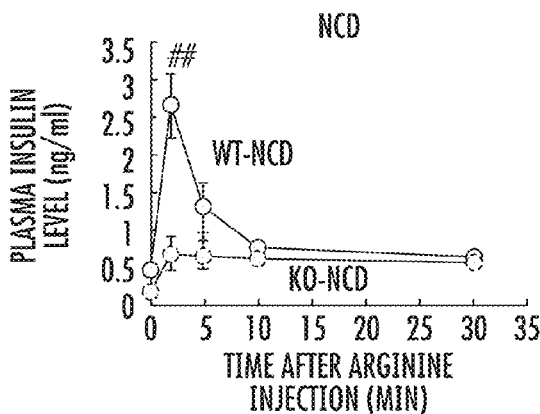
Figures 2, 2F:
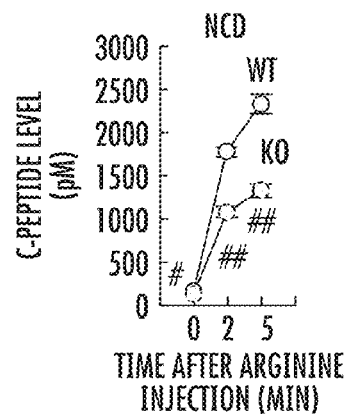
Figures 1, 2G:
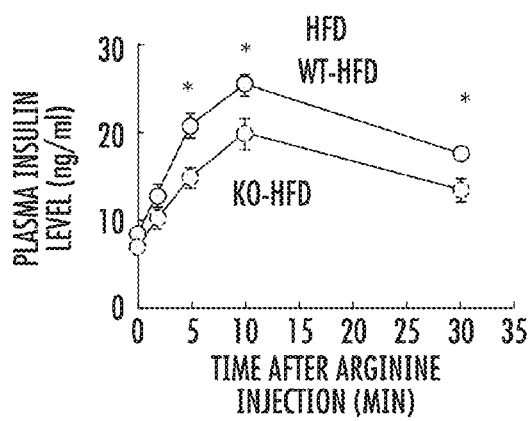
Figures 2, 2G:
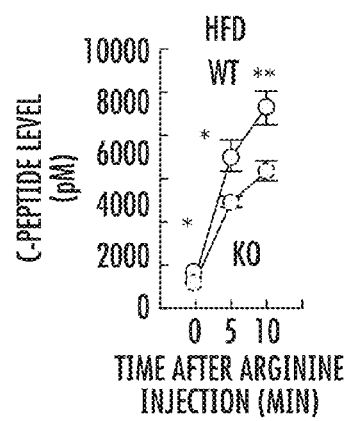

Unexpectedly, both lean/chow-fed and obese/HFD CX3CR1 KO mice developed glucose intolerance compared to wild type (WT) mice upon oral glucose administration, and this effect was exacerbated in the obese state (FIGS. 2A-1 to 2A-2). Despite the glucose intolerance, these mice exhibited normal insulin sensitivity, as shown by insulin tolerance testing (FIGS. 2B-1 to 2B-2), suggesting that a defect in insulin secretion was the cause of the hyperglycemia. To assess this, circulating insulin and C-peptide levels were measured during the oral glucose tolerance tests (OGTTs). Lean chow-fed and obese HFD KO mice displayed decreased insulin and C-peptide secretion with normal GLP1 levels (FIGS. 2C-1 to 2C-3, 2D-1 to 2D-3, and FIG. 8), compared to their WT counter parts, indicating that CX3CR1 deficiency causes a beta cell insulin secretory defect. Interestingly, the glucose intolerance and the defect in insulin secretion in the CX3CR1 KO mice was more pronounced after an intravenous (IV) glucose challenge, and the differences between WT and KO mice were quantitatively greater than after oral glucose (FIGS. 2E-1 to 2E-2). Furthermore, insulin secretion provoked by intraperitoneal (IP) arginine administration was reduced in both lean/chow-fed and obese/HFD CX3CR1 KO mice (FIGS. 2F-1 to 2F-2 and 2G-1 to 2G-2) further indicating that CX3CR1 deficiency causes a beta cell insulin secretory defect.

Figures 1, 2H:
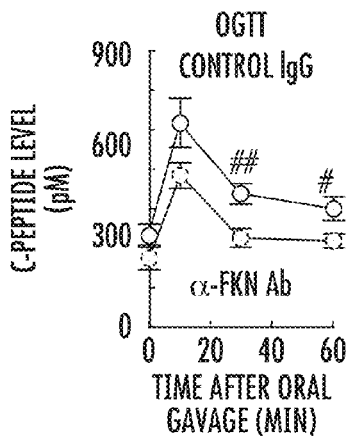
Figures 2, 2H:
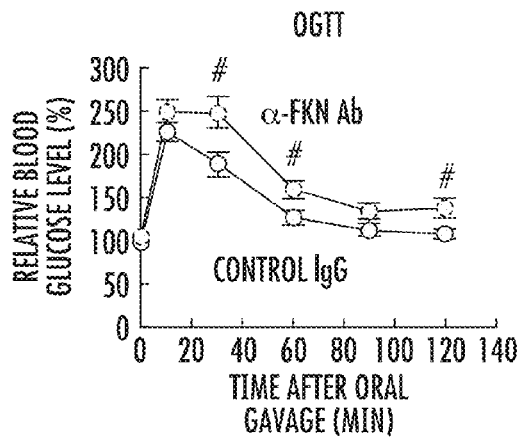

In complementary experiments, anti-FKN antibodies were injected into mice to neutralize circulating FKN. This led to decreased C-peptide levels and glucose intolerance (FIGS. 2H-1 to 2H-2), fully consistent with the results in the KO mice, indicating that ongoing stimulation of CX3CR1 is required for normal insulin secretion and glycemic control.

Example 3

Figure 3A:
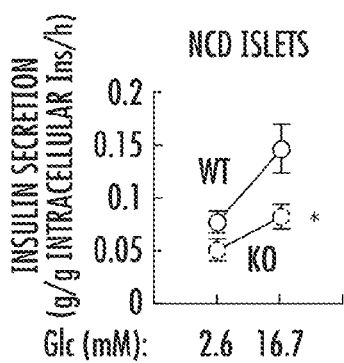
Figure 3B:
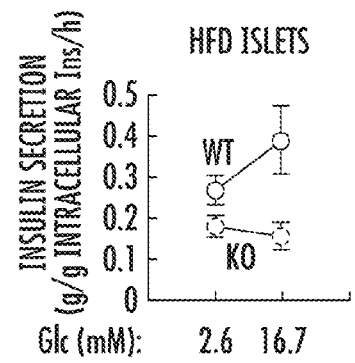
Figure 3C:
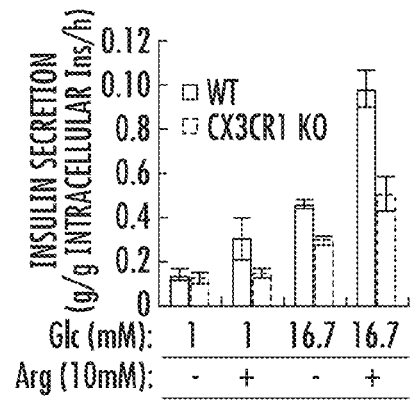
Figures 1, 3D:
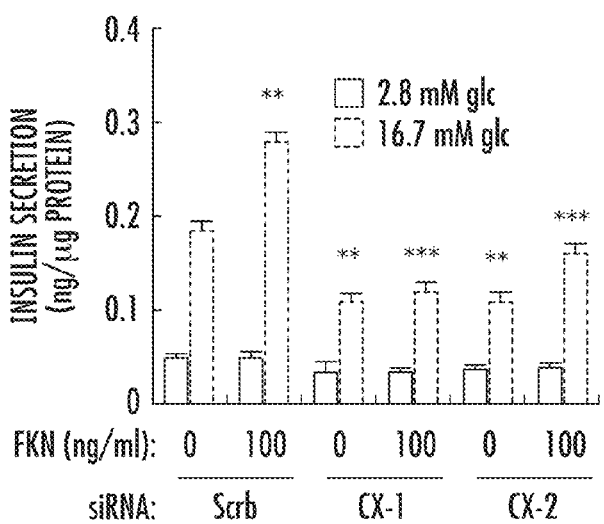
Figures 2, 3D:
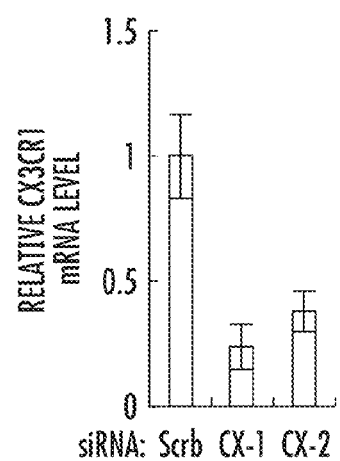
Figures 1, 3H:
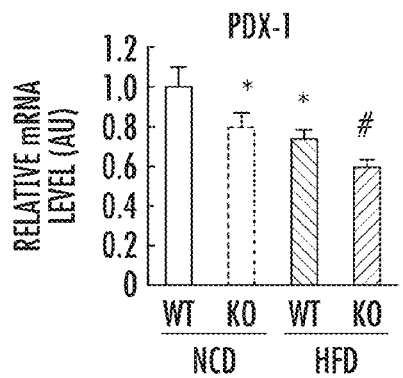
Figures 2, 3H:
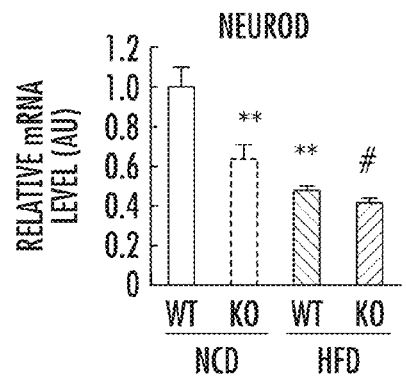
Figures 3, 3H:
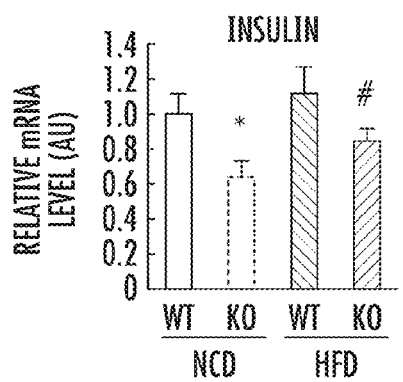

CX3CR1 KO Islets Display Reduced Insulin Secretion with Decreased Expression of Genes Associated with Beta Cell Function To directly test beta cell function, and to determine whether the in vivo insulin secretory defects are primary or secondary, in vitro systems on isolated islets and Min6 cells were carried out. First, to directly test the function of CX3CR1 in beta cells, insulin secretion was measured under static incubation conditions by isolated islets obtained from chow and HFD WT and CX3CR1 KO mice. As seen in FIG. 3A, the KO islets exhibited a marked decrease in GSIS which was more profound in islets obtained from HFD KO mice (FIG. 3B). Moreover, CX3CR1 KO islets exhibited reduced insulin secretion in response to arginine (FIG. 3C), consistent with the in vivo results seen in FIGS. 2F-1 to 2F-2. To demonstrate the cell autonomous effects of CX3CR1 on GSIS in another way, and to show that they are independent of in vivo developmental issues, RNAi interference was used to deplete CX3CR1 in Min6 cells in vitro (FIGS. 3D-1 to 3D-2). Two different anti-CX3CR1 siRNAs led to CX3CR1 knockdown and both attenuated GSIS and abrogated FKN effects on insulin secretion. Time-dependent insulin secretions were subsequently measured in WT and KO islets using perifusion analysis. The KO islets demonstrated significantly lower insulin secretion rates compared to WT in response to both high glucose and GLP1 stimulation (FIG. 3E). Interestingly, oxygen consumption rates by WT and CX3CR1 KO islets were comparable (FIGS. 9A to 9C), implying that CX3CR1 KO does not affect metabolic pathways or mitochondrial respiration. These in vitro experiments demonstrate that the effects of CX3CR1 deletion are cell autonomous and not secondary to other in vivo events.

To test that the affect of CX3CR1 KO is intrinsic to the islet in vivo, CX3CR1 KO and WT islets were transplanted into the kidney capsule in streptozotocin (STZ)-induced diabetic mice. As seen in FIG. 3F, transplantation of WT islets had a greater effect to lower glucose levels compared to transplantation of the KO islets. This was further confirmed by measurements of insulin secretion, which showed greater basal and insulin stimulated insulin levels in the STZ mice transplanted with WT islets compared to the STZ mice receiving the KO islets (FIG. 3G). Thus, the insulin secretory defect in CX3CR1 KO islets is mediated by alterations in islet function independent of extra-islet mechanisms. Taken together, these data indicate that the beta cell FKN/CX3CR1 system is necessary for normal insulin secretory function in response to glucose, arginine, and GLP1, both in vitro and in vivo.

Figure 10:
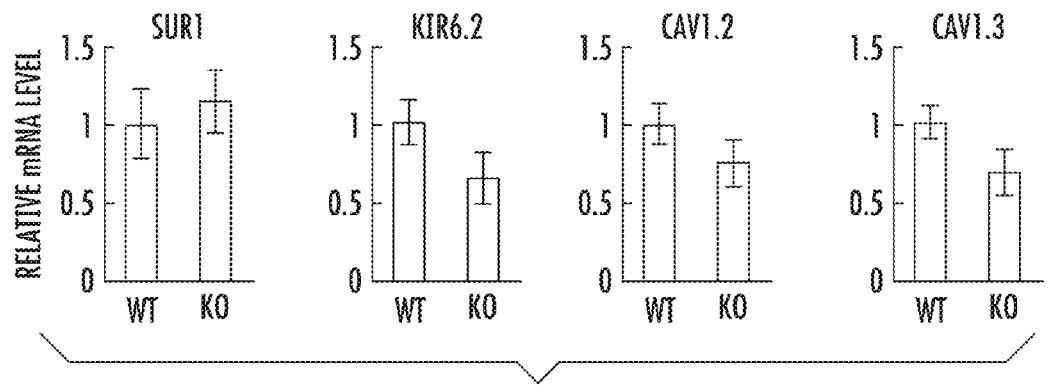
FIG. 10. mRNA expression of components of ATP-dependent potassium channels or voltage-gated calcium channels in WT or CX3CR1 KO islets (related to FIGS. 3A to 3H-6)

To test whether the insulin secretory defect in CX3CR1 KO islets is associated with altered gene expression, quantitative RT-PCR analyses were performed. As shown in FIGS. 3H-1 to 3H-6, the KO islets expressed lower levels of genes involved in normal beta cell secretory function such as PDX-1, NeuroD, insulin, Glut2, and urocortin3. Moreover, CX3CR1 KO islets exhibited reduced expression of Connexin 36 (FIGS. 3H-1 to 3H-6), a gap junction component involved in beta cell communication allowing the synchronization of islet responses to metabolic signals (Calabrese et al., 2003; Carvalho et al., 2010; Speier et al., 2007). Furthermore, expression of some components of ATP-dependent potassium channels (Kir6.2) or L-type voltage-gated calcium channels (Cav1.2 and Cav1.3) was reduced in CX3CR1 KO islets although this did not reach statistical significance (FIG. 10). Thus, the insulin secretory defect in CX3CR1 KO islets is associated with reduced expression of genes involved in beta cell function and communication.

Example 4

Histologic Studies of WT and CX3CR1 KO Islets

Figure 4A:
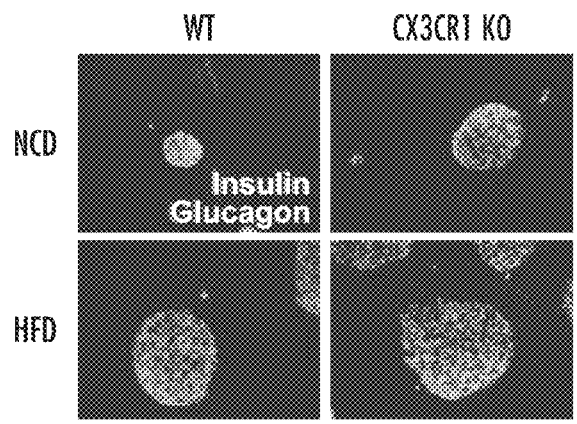
Figure 4B:
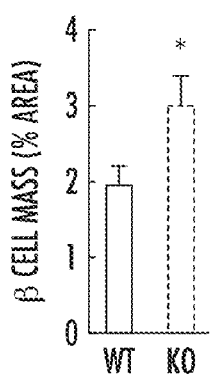
Figure 4C:
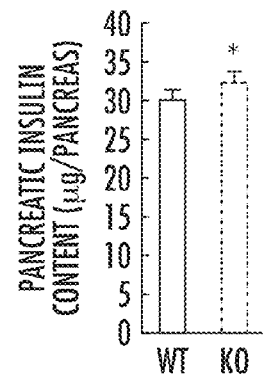
Figure 4D:
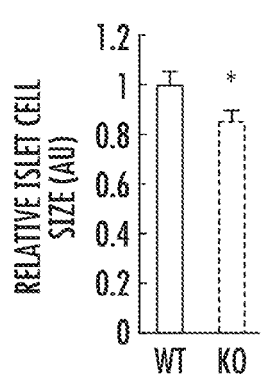
Figure 4E:
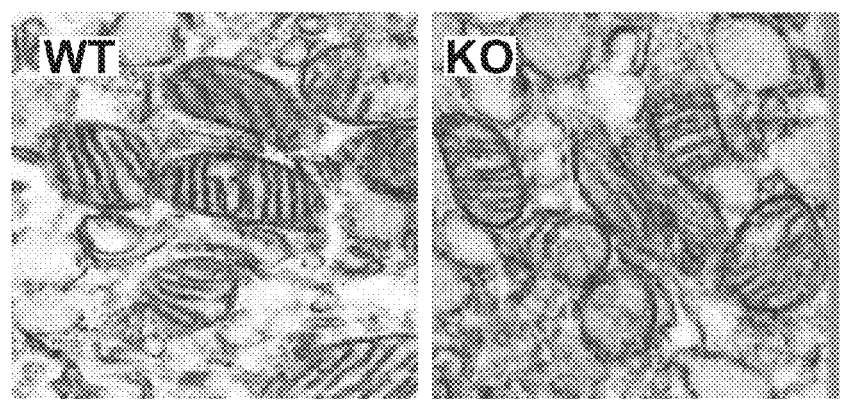
Figures 1, 4F:
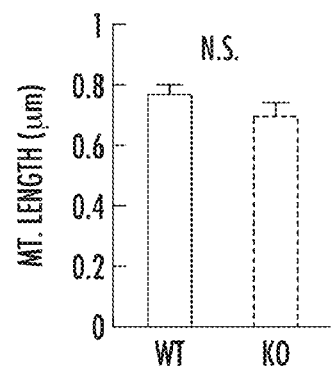
Figures 2, 4F:
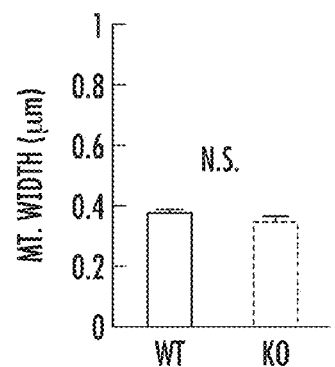
Figures 3, 4F:
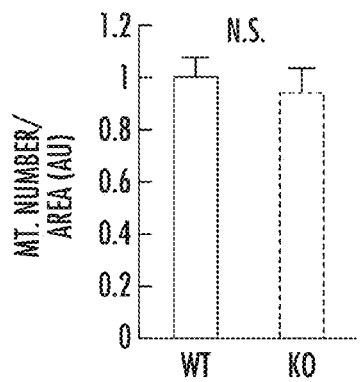
Figures 4, 4F:
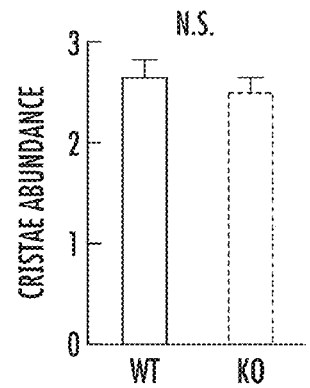
Figure 11A:
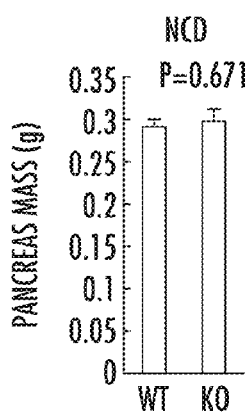
FIGS. 11A to 11C. Insulin content of WT or CX3CR1 KO islet and total pancreas mass (related to FIGS. 4A to 4I).
Figure 11B:
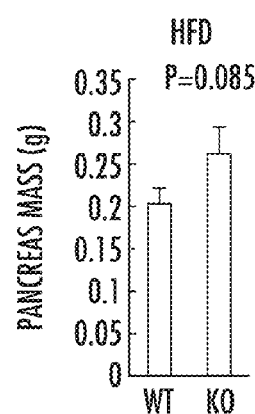
Figure 11C:
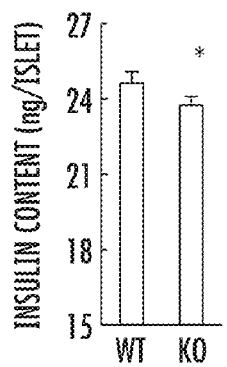

To determine whether CX3CR1 deletion affects islet development, immunohistologic (IHC) studies were conducted and the expected effect of HFD to increase islet size (Maclean and Ogilvie, 1955; Pick et al., 1998) was found. However, under both chow and HFD conditions, the islets were larger in the KO mice (FIG. 4A). This was accompanied by a significant ($P<0.05$) increase in beta cell mass, as measured by morphometric analyses of insulin positive islet cells (FIG. 4B), and a corresponding increase in total pancreatic insulin content (FIG. 4C, FIGS. 11A and 11B). These results show that CX3CR1 KO mice have sufficient beta cells and insulin, indicating that the in vivo phenotype is due to a defect in coupling extracellular signals to the insulin secretory machinery. Interestingly, the average beta cell size was decreased in the KO islets (FIG. 4D), showing that the enhanced islet mass was due to an increased number of smaller beta cells. It has been reported that smaller beta cells display decreased GSIS activity (Giordano et al., 1993; Pende et al., 2000). Consistent with this, when similar sized WT and CX3CR1 KO islets were selected for comparison, a small but significant decrease in insulin content per islet was seen in the CX3CR1 KO group (FIG. 11C).

Figures 3, 3H, 4:
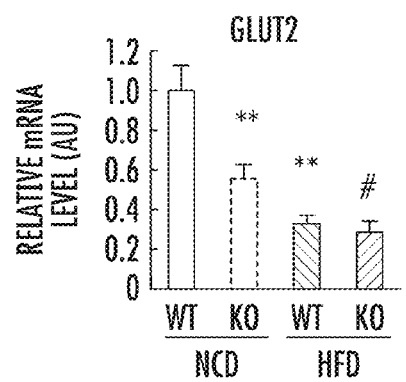
Figures 3, 3H, 4, 5:
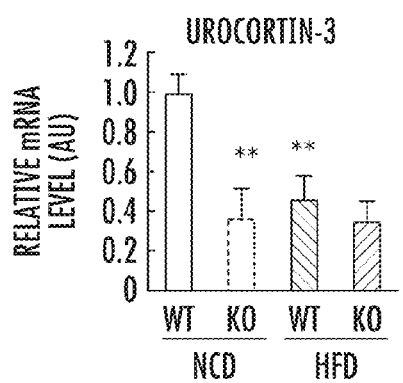
Figures 3, 3H, 4, 5, 6:
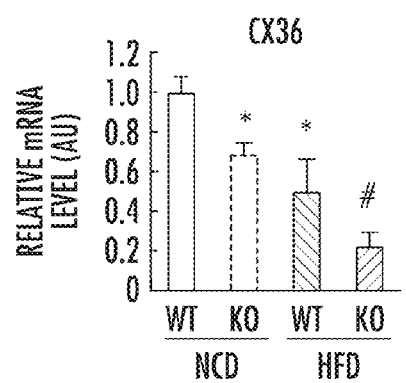
Figures 1, 4G:
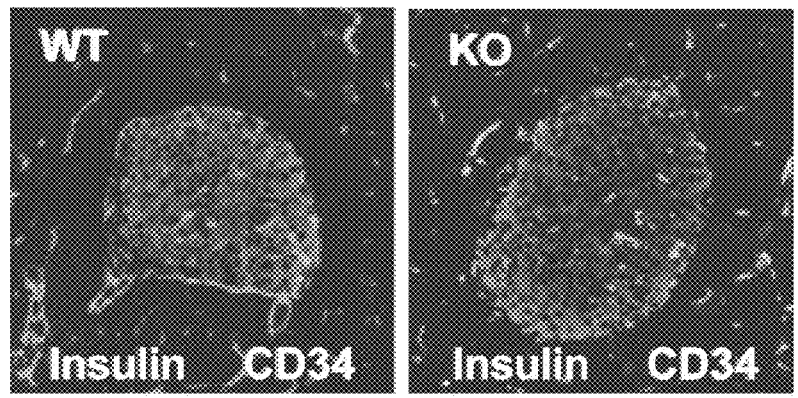
Figures 2, 4G:
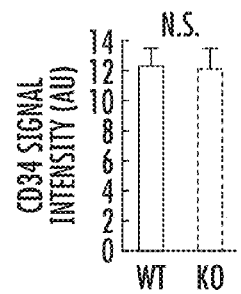
Figure 9A:
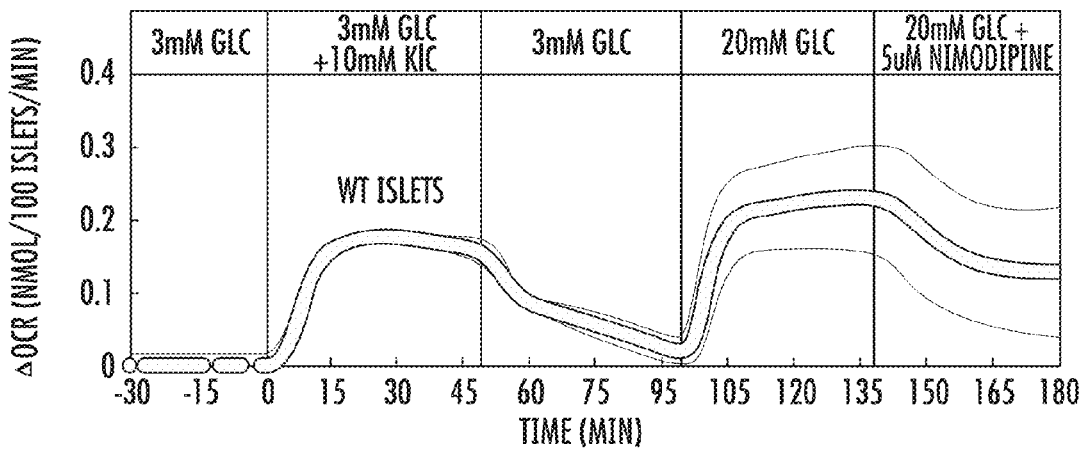
FIGS. 9A to 9C. Oxygen consumption in islets by FKN during perifusion (related to FIGS. 3A to 3H-6).
Figure 9B:
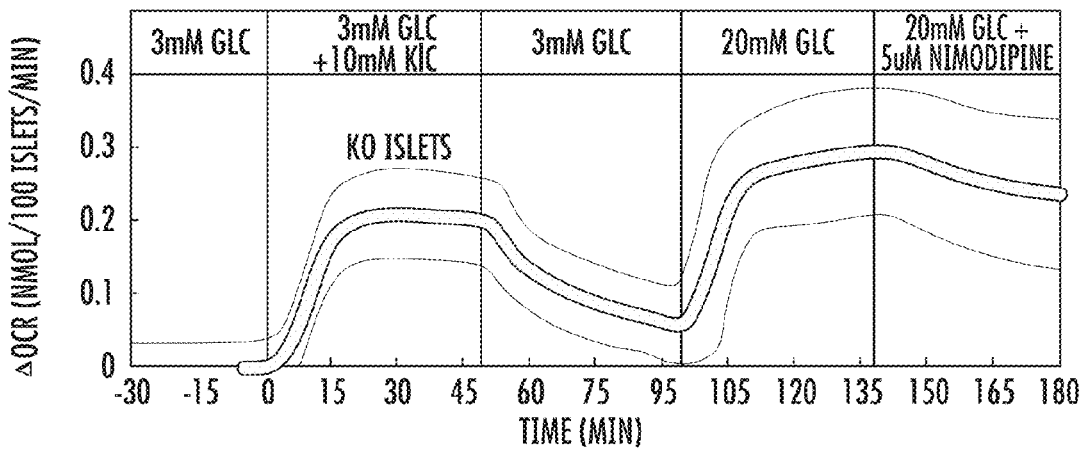
Figure 9C:
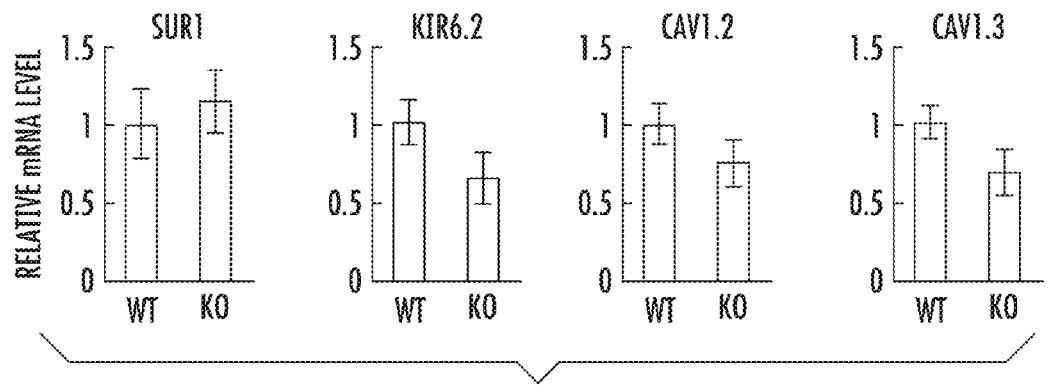

The histologic analysis also showed that the morphologic features of the WT and KO islets, such as predominance of insulin positive beta cells in the core mantled by glucagon positive alpha cells, was unaffected by the KO (FIG. 4A). To assess mitochondria in CX3CR1 KO islets, ultramicroscopic analysis was performed using electron microscopy. As seen in FIGS. 4E and 4F-1 to 4F-4, morphology, size, number, and cristae abundance of mitochondria were comparable in WT and CX3CR1 KO beta cells, consistent with the normal oxygen consumption rate in the CX3CR1 KO islets (FIGS. 9A to 9C). Formation of a proper microvascular network within islets is essential for adequate insulin secretion (Eberhard et al., 2010; Lammert et al., 2003), and since FKN/CX3CR1 can modulate angiogenic pathways, vascular density within the islets was assessed by staining for the endothelial marker CD34. As seen in FIGS. 4G-1 to 4G-2, CD34 staining was the same in CX3CR1 KO and WT islets. Finally, total pancreas mass in chow-fed or HFD CX3CR1 KO mice was comparable to WT (FIGS. 11A to 11C). Together, the results suggest that the defective insulin secretion in CX3CR1 KO mice was not due to gross developmental defects, mitochondrial dysfunction, or defective intra-islet vascularization.

Figure 4H:
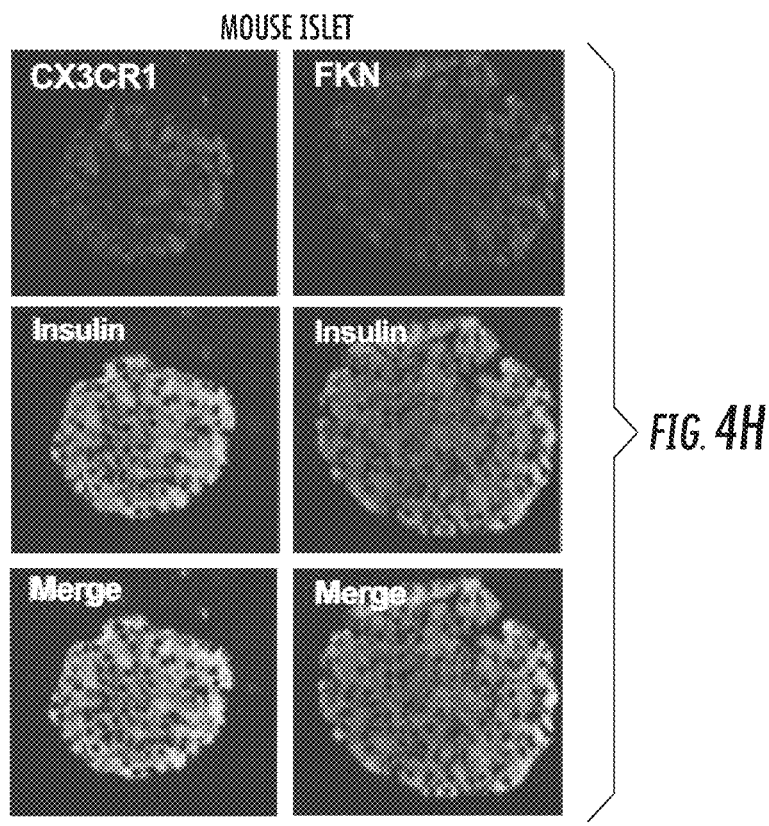
Figure 4I:
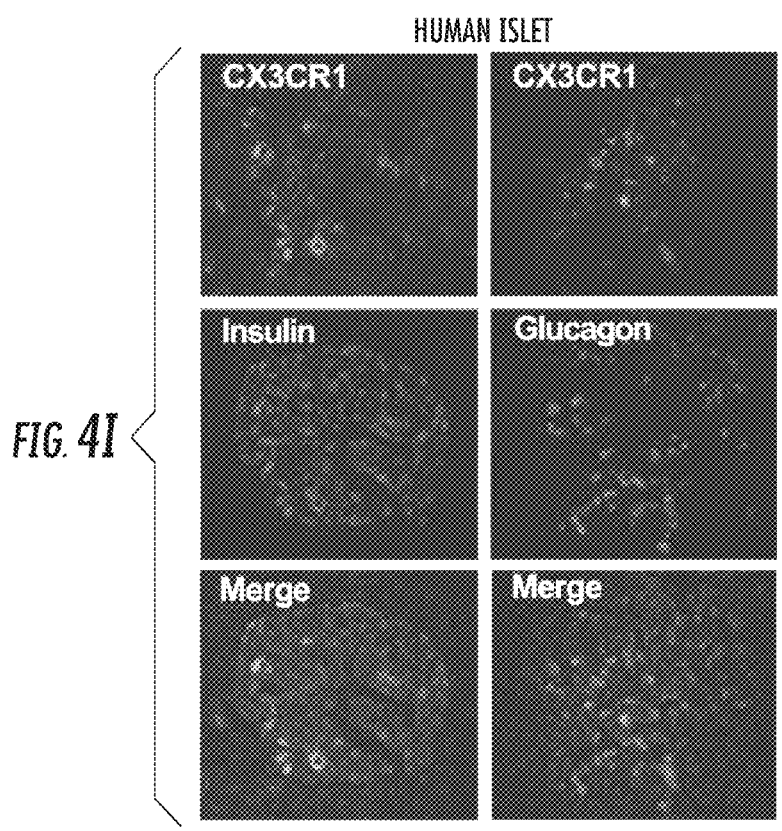
Figure 12:
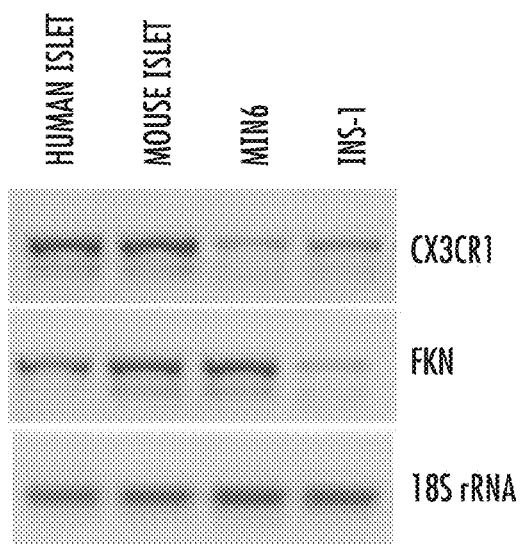
FIG. 12. CX3CR1 and FKN are expressed in human and mouse islets, and Min6 and INS-1 mouse and rat beta cell lines (related to FIGS. 4A to 4I). Semi-quantitative RT-PCR analysis of CX3CR1 and FKN expression in human and mouse islets, Min6 and INS-1 cells.

As shown in FIG. 4H, IHC revealed that FKN and CX3CR1 are highly expressed in insulin-positive beta cells in mouse islets. Similarly, in human islets, CX3CR1 was expressed in beta cells, but not in glucagon-positive alpha cells (FIG. 4I). RT-PCR analyses revealed that both the receptor and FKN are expressed in isolated human and murine islets, as well as in the Min6 (mouse) and INS-1 (rat) beta cell lines (FIG. 12).

Example 5

In Vitro and In Vivo FKN Treatment

Figure 5F:
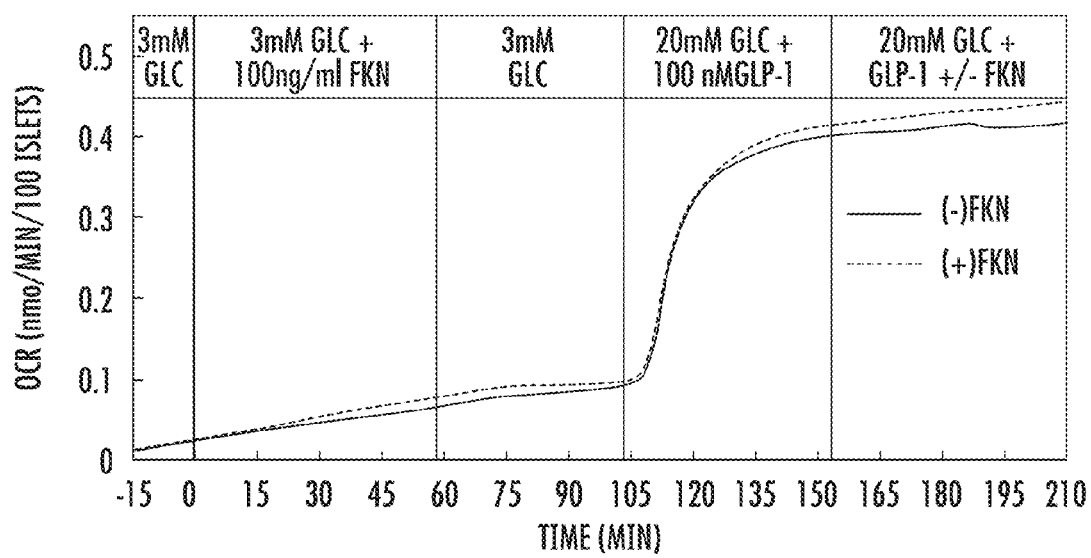
Figure 5G:
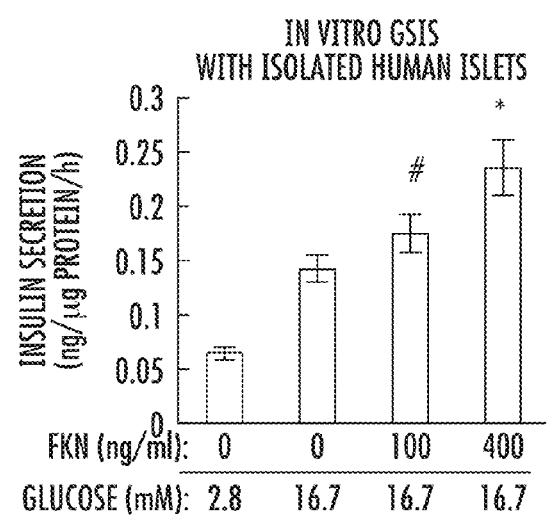
Figure 13:
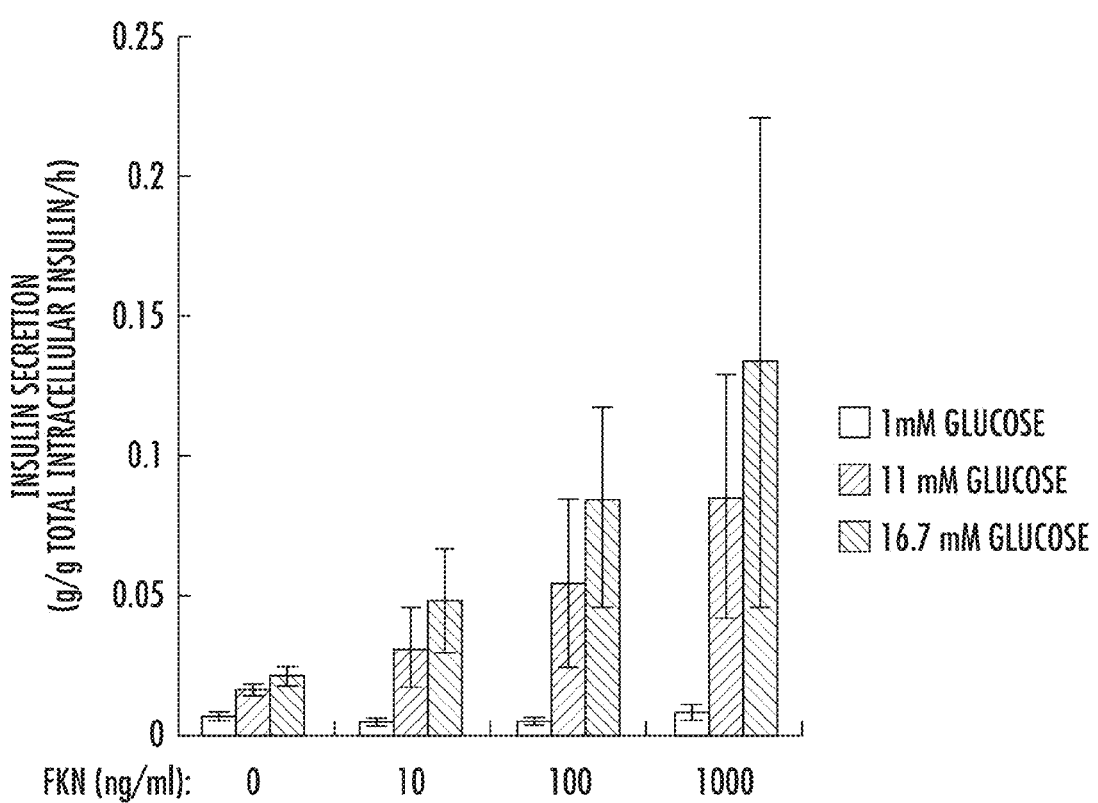
FIG. 13. FKN stimulates GSIS in a dose-dependent manner. Primary mouse islets were stimulated with intermediate (11 mM) or high glucose (16.7 mM) concentration in different concentrations of FKN (10-1000 ng/ml) (related to FIGS. 5A to 5G).

To provide a further test of the overall concept, WT and CX3CR1 KO mice were treated with acute administration of the 84 amino acid soluble chemokine portion of circulating mouse FKN. This led to improved glucose tolerance in the WT mice (FIG. 5A), but was without effect on glucose levels in the KO animals (FIG. 5B). Importantly, in vivo FKN administration caused an increase in insulin secretion in the WT mice, but not in the KOs (FIG. 5C, FIG. 13). Isolated WT and CX3CR1 KO islets were also treated with soluble FKN and a marked 58% increase in GSIS in WT islets with no effect in the KO islets was found (FIG. 5D). FKN also significantly potentiated glucose plus GLP1-induced insulin secretion in perifused primary mouse islets (FIG. 5E), but did not effect oxygen consumption (FIG. 5F). These in vivo and in vitro results demonstrate that FKN effects are direct and are CX3CR1-dependent. To demonstrate the translatability of these findings to human beta cells, studies in isolated human islets were conducted. As seen in FIG. 5G, treatment of human islets with human FKN led to a dose responsive increase in GSIS with a 65% increase at the maximal concentration. Thus, the potentiating effects of FKN are quantitatively similar in mouse and human islets.

Example 6

Effects of FKN Treatment on Beta Cell Signaling

Figures 1, 6A:
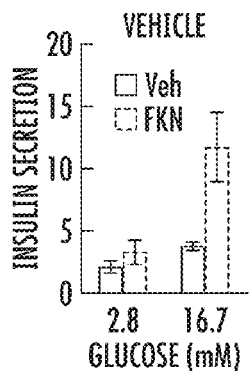
Figures 2, 6A:
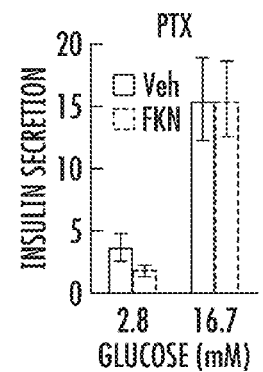
Figures 3, 6A:
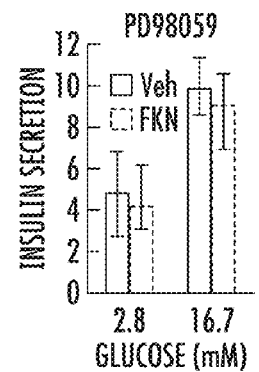
Figures 4, 6A:
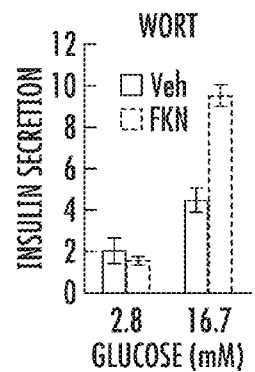
Figure 6B:
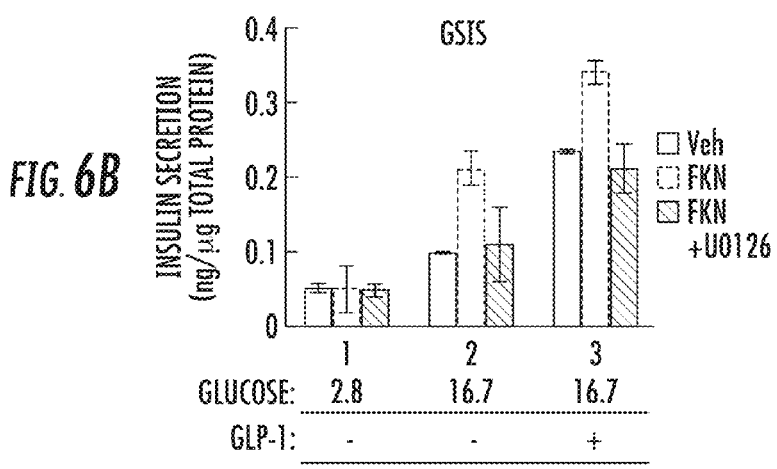
(FIG. 6B) GSIS test using Min6 cells with or without FKN (100 ng/ml) or U0126 (10 µM). Mean+/−SEM.
Figure 14:
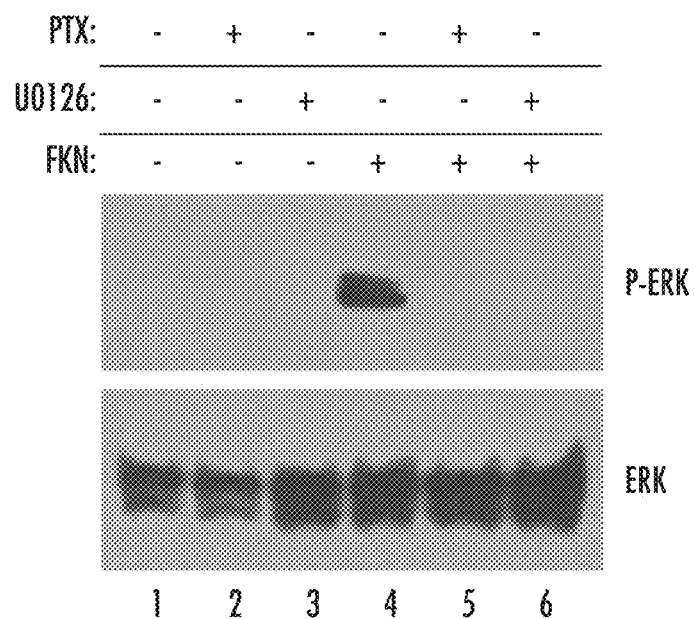
FIG. 14. FKN stimulates ERK phosphorylation in a PTX-sensitive manner (related to FIGS. 6A-1 to 6Q-4). Min6 cells were pre-treated with DMSO (control), U0126 (10 µM), or PTX (250 ng/ml) for 15 min, and then incubated with or without FKN (100 ng) for 15 min. Cells were harvested and subjected to western blot.

To determine the pathways by which FKN/CX3CR1 regulates insulin secretion, GSIS was measured in isolated islets treated with inhibitors of Gαi (pertussis toxin), PI3K (Wortmannin), and MEK (PD98059) at low and high glucose levels. FKN-stimulated insulin secretion was inhibited by pertussis toxin and the MEK inhibitor, but not by Wortmannin (FIGS. 6A-1 to 6A-4). Consistent with these results, FKN stimulated ERK phosphorylation in a Gαi and MEK dependent fashion (FIG. 14), and inhibition of MEK suppressed FKN potentiation of glucose and GLP1-induced insulin secretion in Min6 cells (FIG. 6B). As seen in FIGS. 6A-1 to 6A-4 and 6B, FKN-stimulated insulin secretion was not evident at 2.8 mM glucose and only occurred when sufficient glucose was provided (16.7 mM), consistent with FIGS. 5A to 5G, which shows that FKN is not a direct insulin secretagogue, but rather, potentiates the effects of other insulin secretory signals such as glucose and GLP1.

Figure 6C:
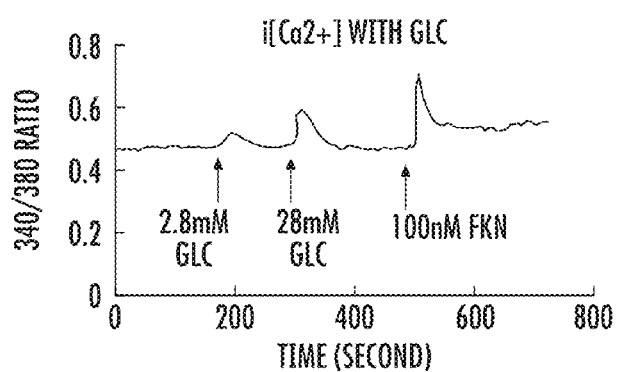
(FIGS. 6C to 6I) Intracellular calcium level in Min6 mouse beta cells in the presence or absence of glucose (FIG. 6C, with glucose.
Figure 6D:
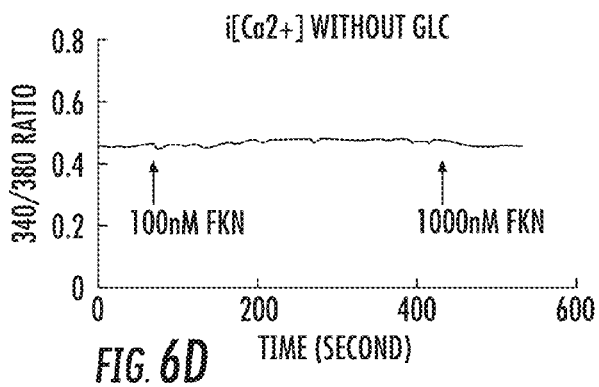
Figure 6E:
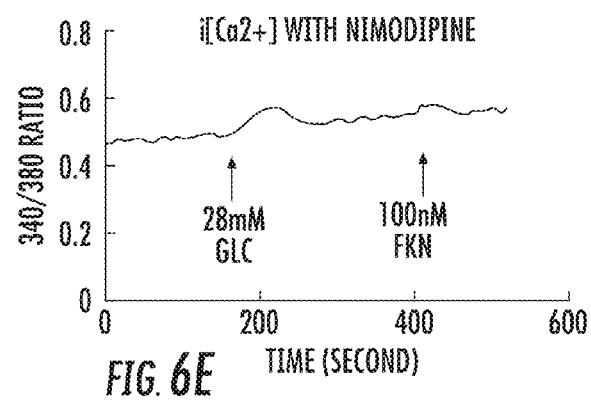
Figure 6F:
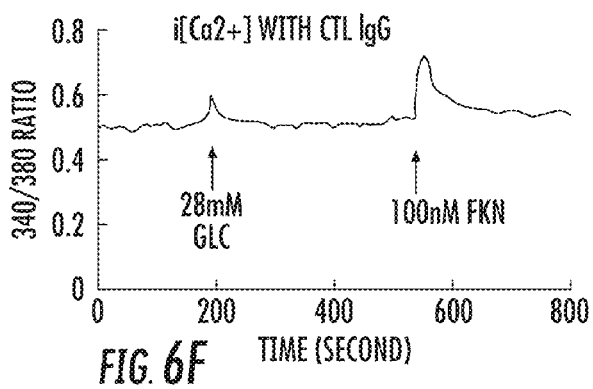
Figure 6G:
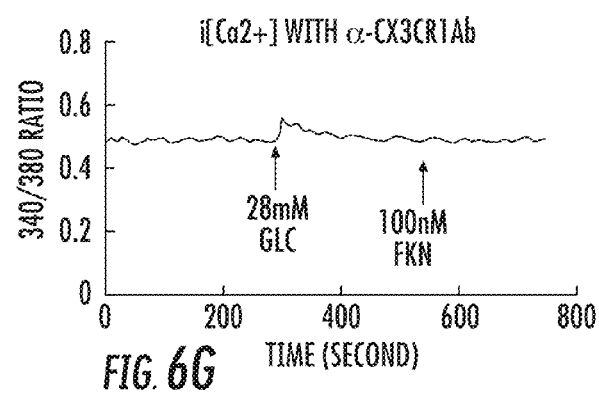
Figure 6H:
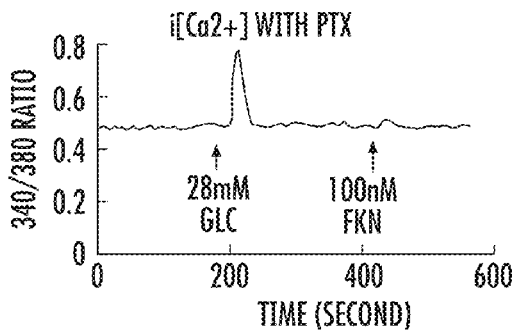
Figure 6I:
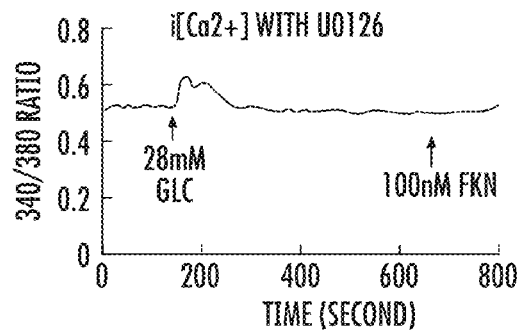
Figures 1, 15A:
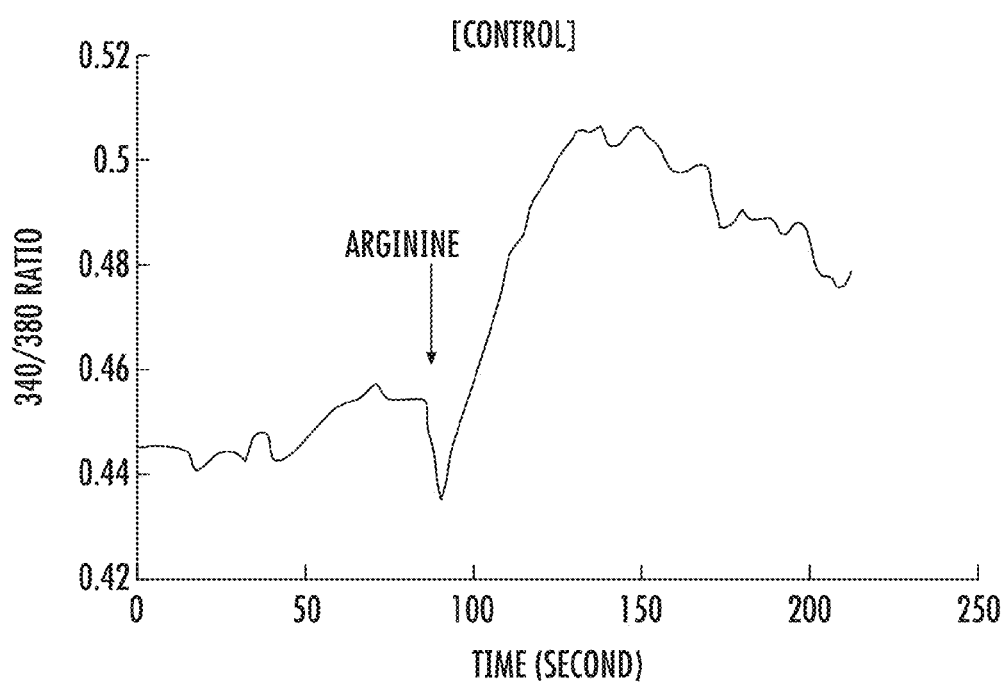
Figures 2, 15A:
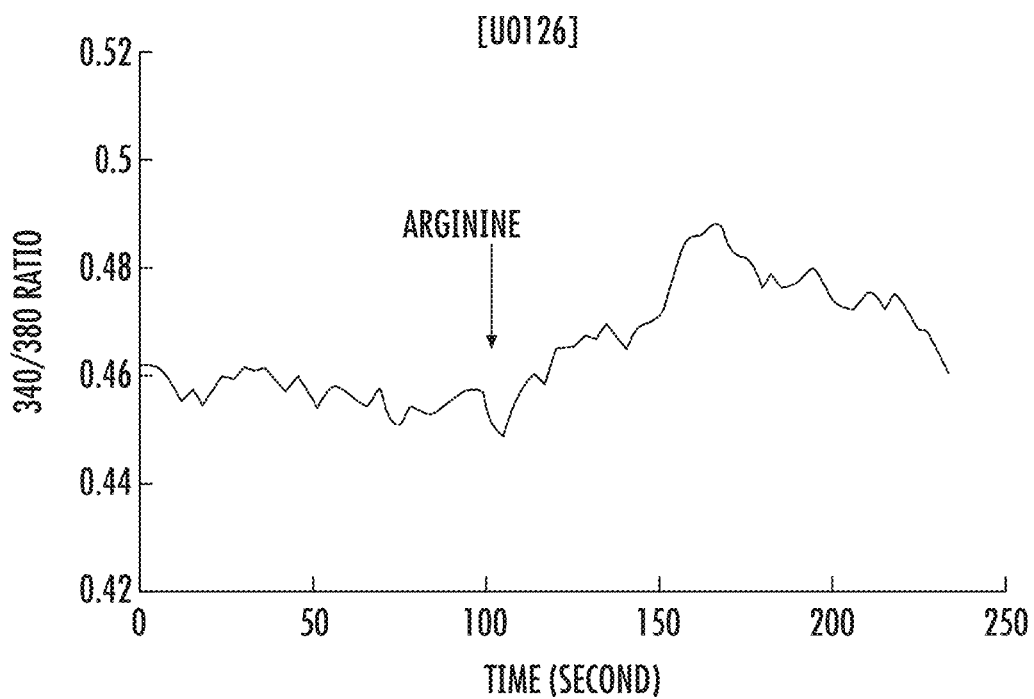
Figures 3, 15A:
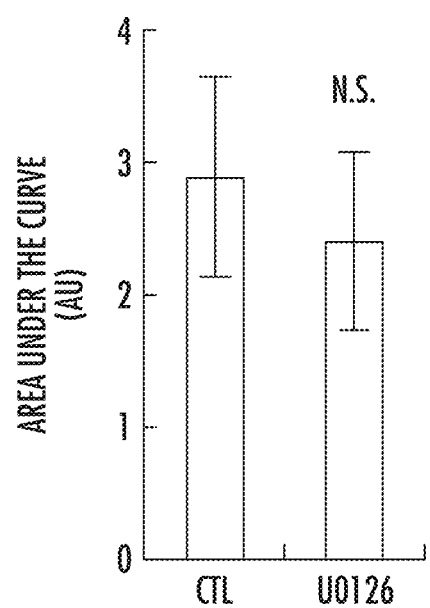
Figures 1, 15B:
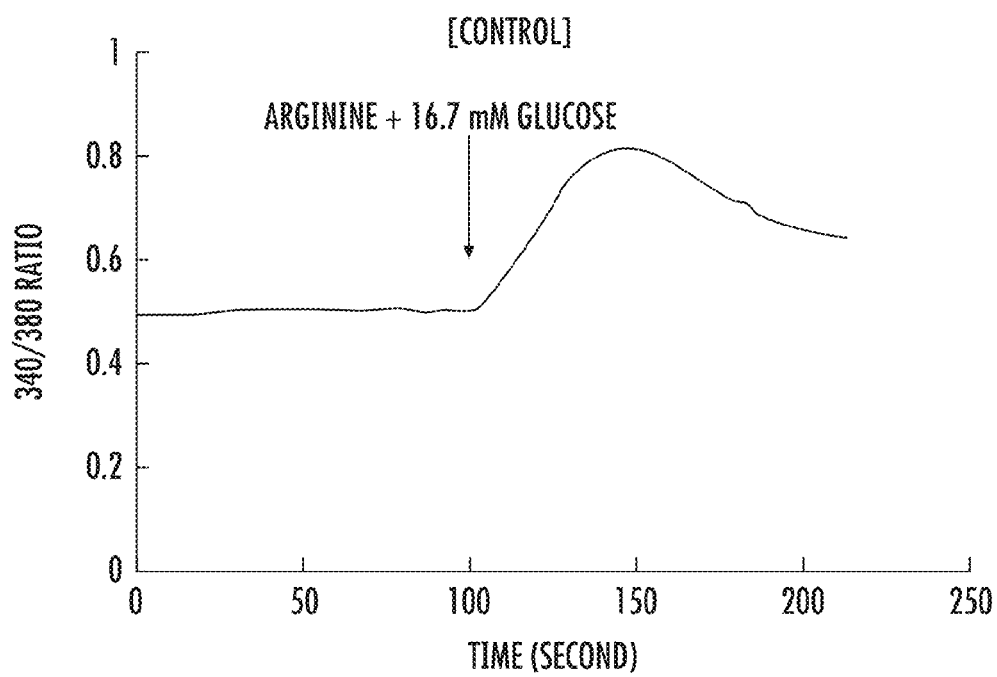
Figures 2, 15B:
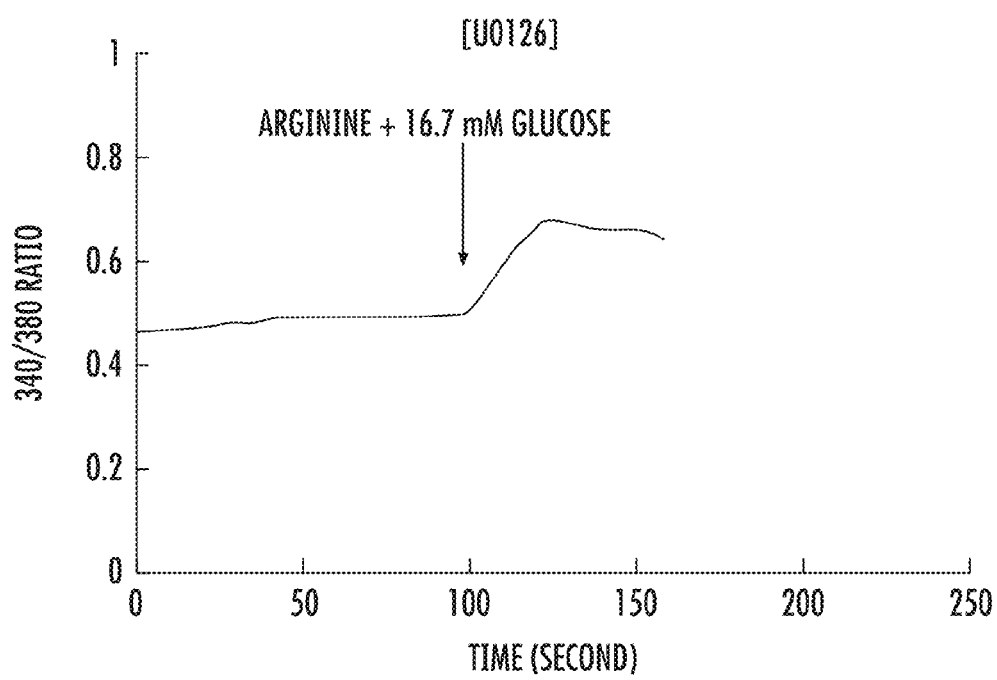
Figures 3, 15B:
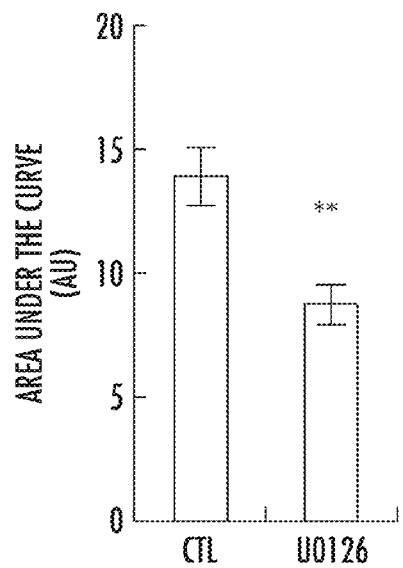
Figure 15C:
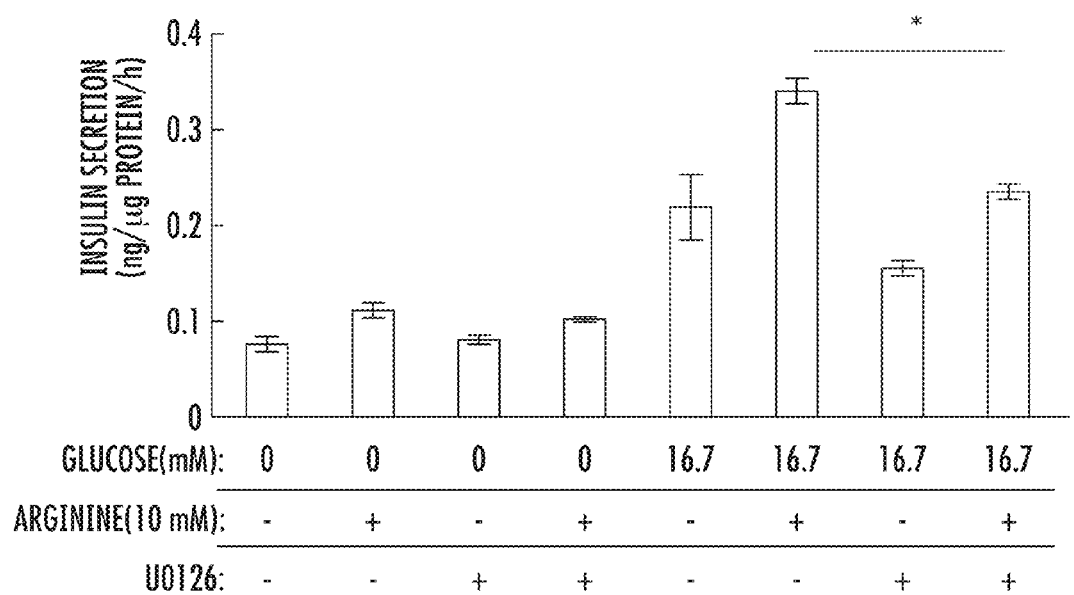

In beta cells, calcium signaling is a critical component of the insulin secretory process (Seino et al., 2011). Since FKN has been shown to increase cytoplasmic calcium levels in macrophages and fibroblasts (Fong et al., 2002; Imai et al., 1997), the FKN effect on intracellular calcium at low or high glucose conditions was measured in Min6 cells. As shown in FIGS. 6C and 6D, FKN increased intracellular calcium levels with high glucose (FIG. 6C), but was without effect in the absence of glucose (FIG. 6D). Interestingly, inhibition of calcium influx by the L type calcium channel inhibitor, nimodipine, blocked both glucose- and FKN-induced intracellular calcium increase, implying that calcium influx is necessary for the FKN effect (FIG. 6E). CX3CR1 neutralization with a specific antibody blocked the FKN-induced intracellular calcium increase, showing that this effect of FKN is mediated by CX3CR1 activation (FIGS. 6F and 6G). Moreover, the effect of FKN on intracellular calcium was blocked by treatment with the pertussis toxin or the MEK inhibitor (FIGS. 6H and 6I), suggesting that a Gαi and MEK-mediated effect plays a mechanistic role in FKN-stimulated insulin secretion. Interestingly, the MEK inhibitor attenuated arginine-induced intracellular $Ca^{2+}$ increase and insulin secretion in Min6 cells, but only in the presence of glucose (FIGS. 15A-1 to 15C).

Figure 6J:
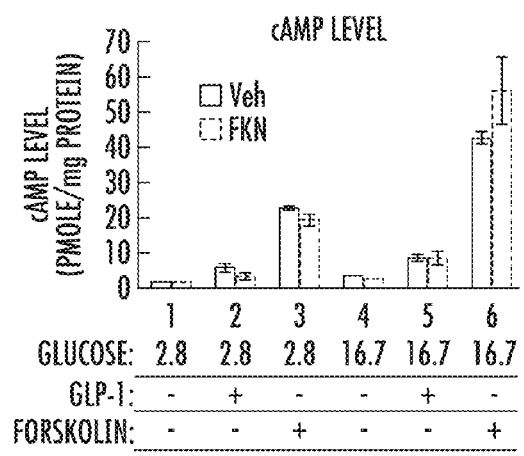
(FIG. 6J) Intracellular cAMP level. Min6 cells were pre-incubated with isobutylmethylxanthine for 30 min, and then treated with GLP1 (100 nM), forskolin (100 µM), or FKN (100 ng/ml) at low (2.8 mM) or high (16.7 mM) glucose conditions for 30 min. Mean+/−SEM.
Figure 6K:
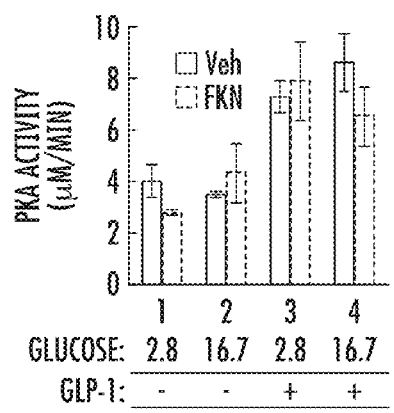
(FIG. 6K) PKA enzymatic activity was measured in Min6 cells incubated in a low (2.8 mM) or high (16.7 mM) glucose condition for 15 min in the presence or absence of GLP1 (100 nM) or FKN (100 ng/ml). Mean+/−SEM.

Part of the effect of glucose and GLP1 to augment insulin secretion involves increases in cyclic AMP levels. Consequently, glucose, GLP1, and forskolin stimulated cyclic AMP levels with and without FKN were measured in Min6 cells (FIG. 6J). Interestingly, FKN was without effect on cyclic AMP concentrations, and consistent with this, PKA activity was also unaffected by FKN treatment (FIG. 6K).

Figures 1, 6L:
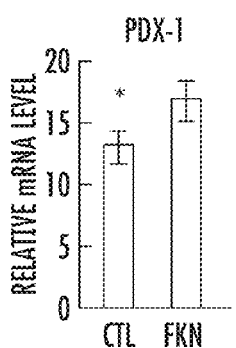
Figures 2, 6L:
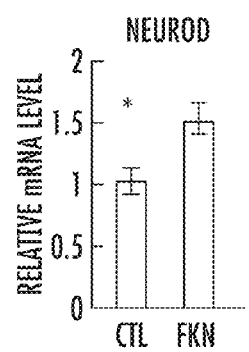
Figures 3, 6L:
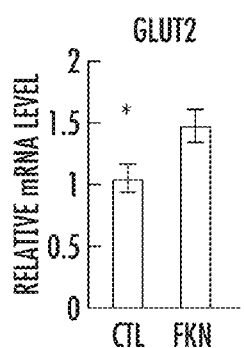
Figures 4, 6L:
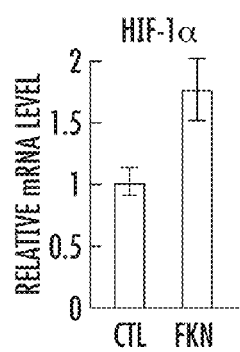
Figure 6M:
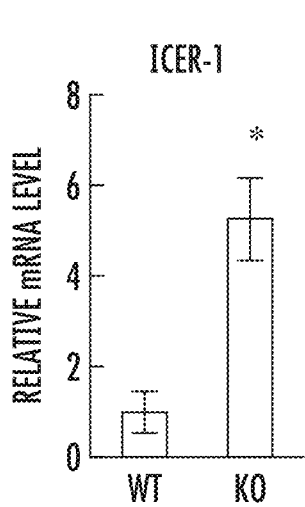
(FIG. 6M) ICER-1 mRNA expression in WT and CX3CR1 KO islets. Mean+/−SEM.
Figure 6N:
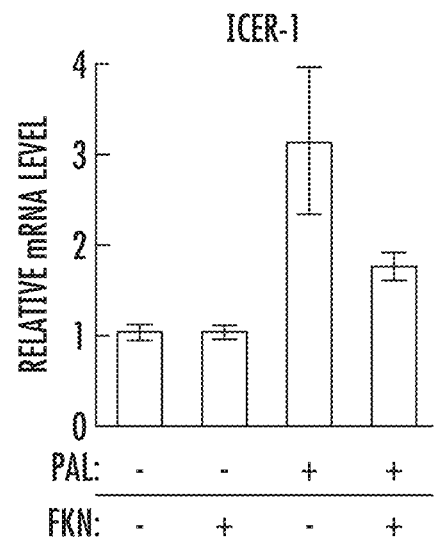
(FIG. 6N) Palmitate-induced ICER-1 expression is suppressed by FKN in Min6 cells. Mean+/−SEM.
Figure 6O:
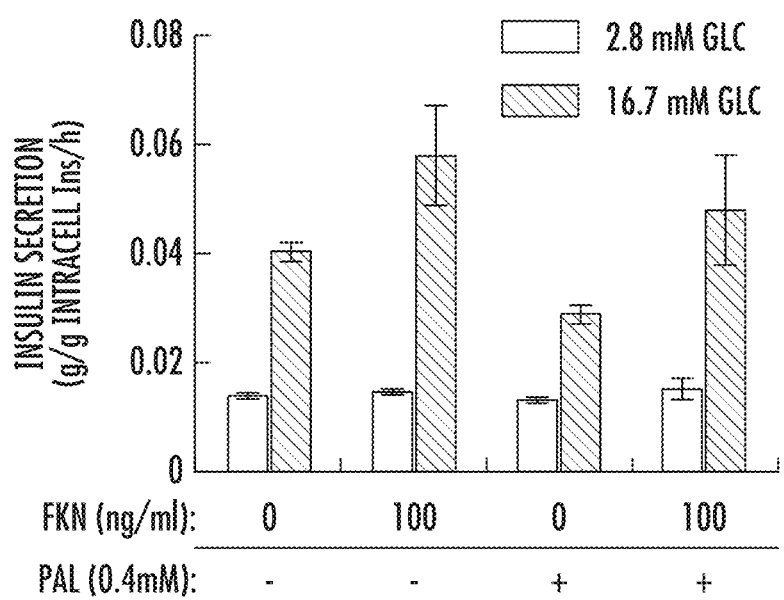
(FIG. 6O) GSIS by Min6 cells treated with palmitate (Pal; 0.4 mM) for 48 h in the presence or absence of FKN (100 ng/ml).
Figures 1, 6P:
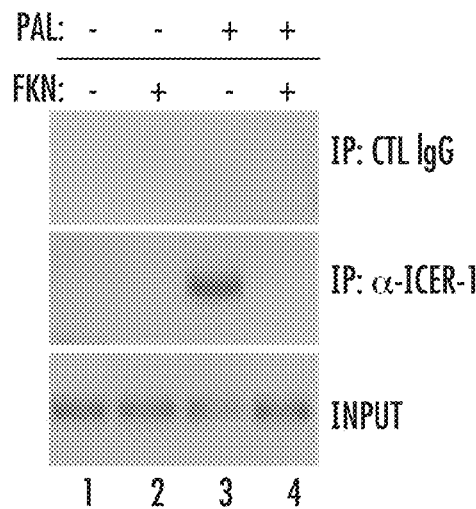
Figures 2, 6P:
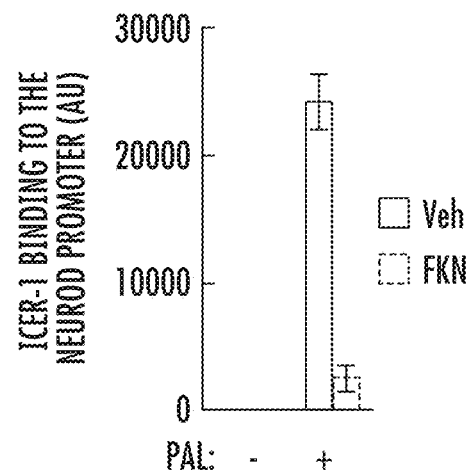
Figures 1, 6Q:
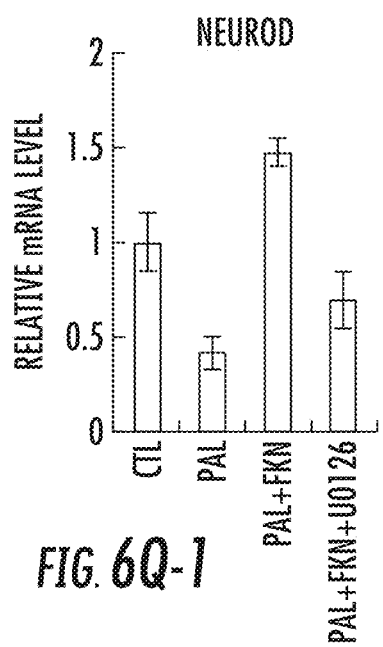
Figures 2, 6Q:
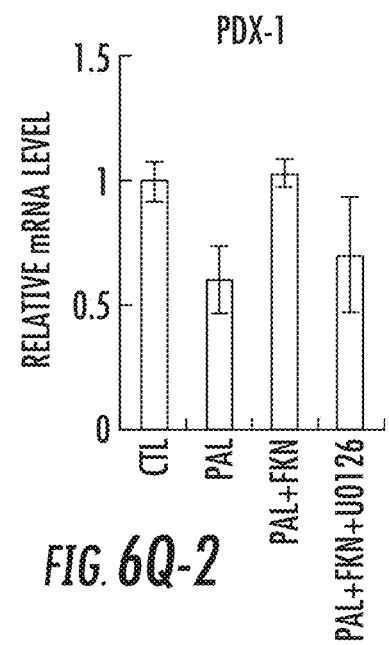
Figures 3, 6Q:
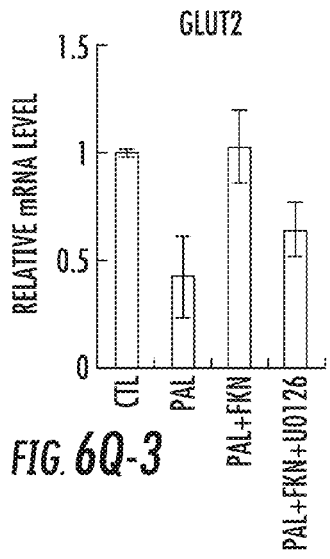
Figures 4, 6Q:
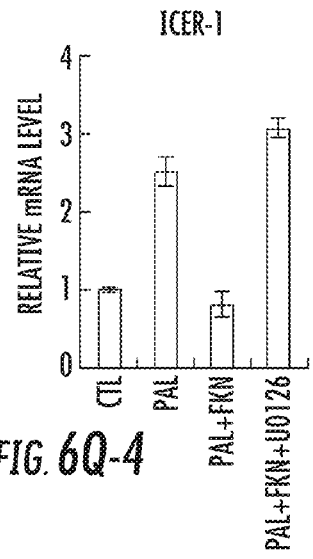

Longer term effects of FKN on islet gene expression were also assessed. Seven (7) days of chronic in vitro treatment of islets with FKN led to increased expression of PDX1, NeuroD, HIF-1α and insulin (FIGS. 6L-1 to 6L-4), and these genes were all down regulated in the CX3CR1 KO islets (FIGS. 3H-1 to 3H-6). Recently, it has been shown that beta cell dysfunction induced by HFD or free fatty acid treatment is, at least partially, mediated by the induction of inducible cyclic AMP early repressor (ICER-1) (Cho et al., 2012; Favre et al., 2011; Hussain et al., 2000; Zhou et al., 2003). Interestingly, ICER-1 expression was highly induced in the CX3CR1 KO islets (FIG. 6M) and FKN treatment abolished palmitate-induced induction of ICER-1 mRNA in Min6 cells (FIG. 6N). Concomitantly, FKN treatment prevented chronic palmitate-mediated inhibition of GSIS (FIG. 6O). Moreover, using chromatin immunoprecipitation experiments, it was found that FKN treatment blocked the effect of palmitate to induce binding of ICER-1 to the NeuroD promoter in Min6 cells (FIGS. 6P-1 to 6P-2). These results suggest that one aspect of the FKN effect on beta cells might involve regulation of genes necessary for the insulin secretory machinery and this could be partially mediated by ICER-1 suppression. To test whether FKN regulation of ICER-1 is associated with MEK signaling pathways, Min6 cells were incubated with palmitate in the presence or absence of FKN and the MEK inhibitor. As shown in FIGS. 6Q-1 to 6Q-4, FKN treatment suppressed palmitate-induced ICER-1 expression while it increased expression of NeuroD, PDX-1 and Glut2; all of the FKN effects were abolished by the MEK inhibitor. These results suggest that FKN suppresses ICER-1 expression through a MEK-dependent pathway.

Figure 16A:
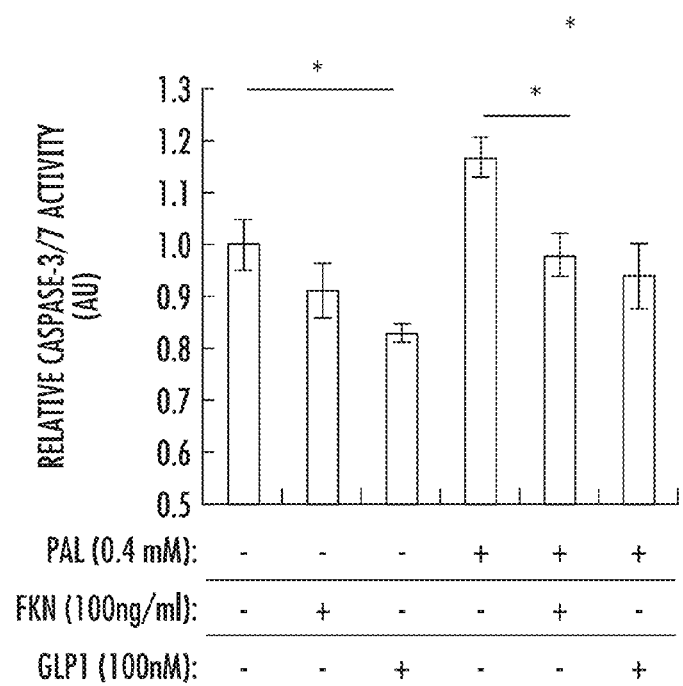
FIGS. 16A to 16F. FKN prevents palmitate-induced beta cell apoptosis in a PI3K-Akt-dependent pathway (related to FIGS. 6A-1 to 6Q-4).
Figure 16B:
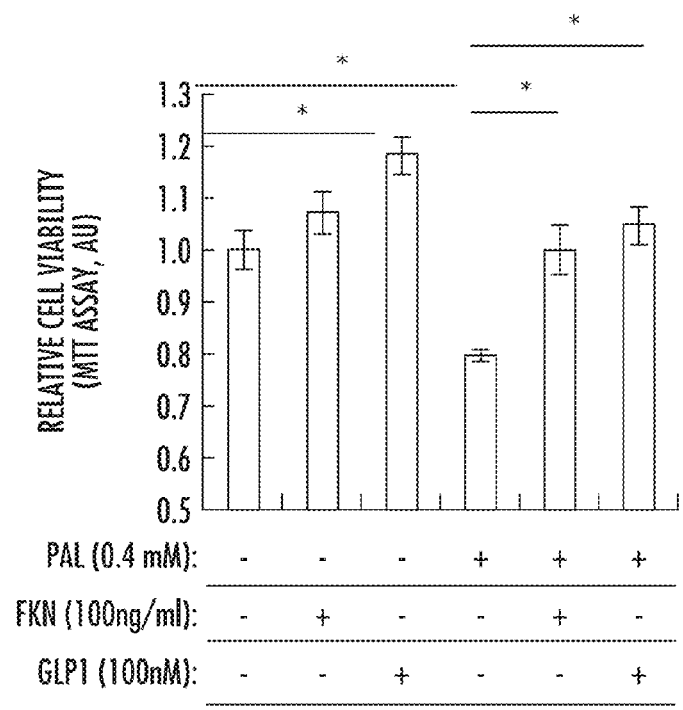
Figure 16C:
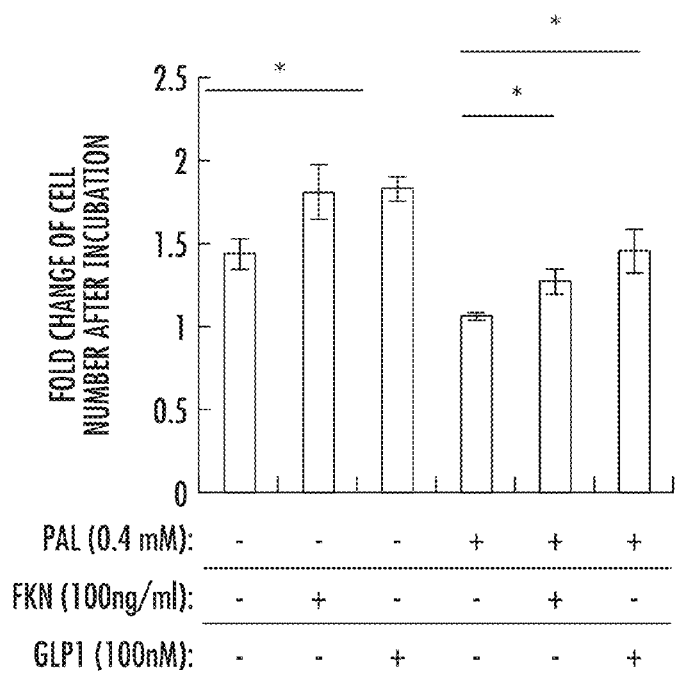
Figure 16D:
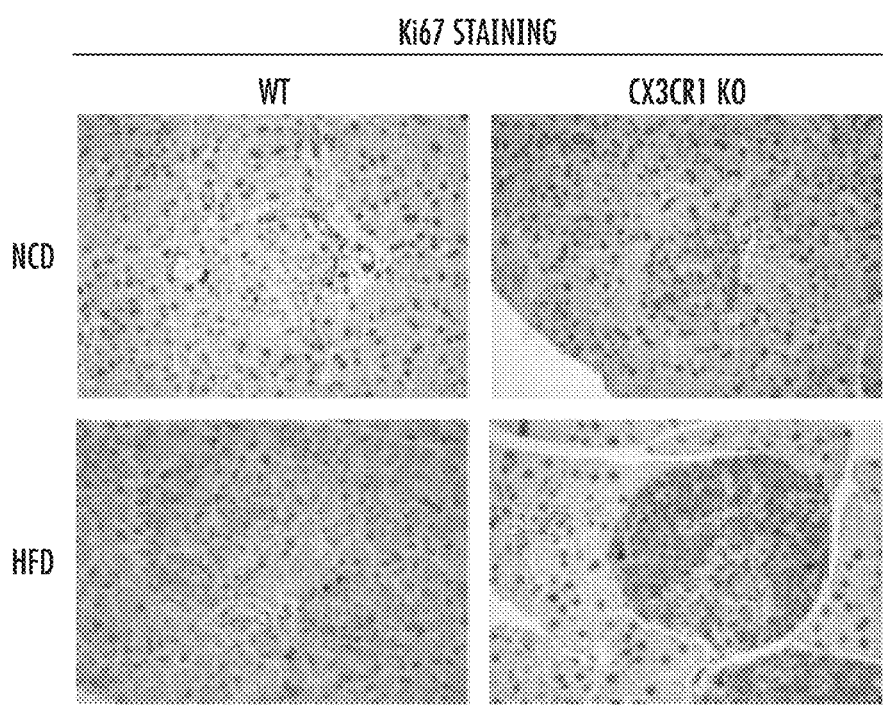
Figure 16E:
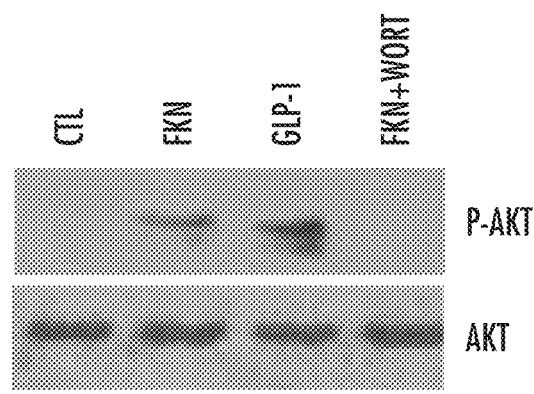
Figure 16F:
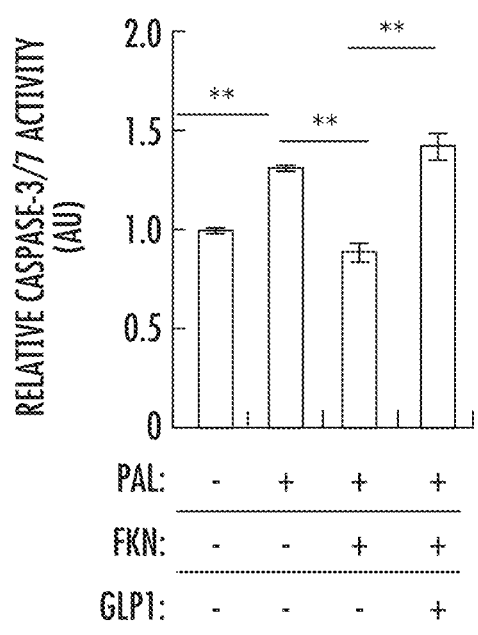

Beta cell failure in type 2 diabetes is associated with loss of beta cell volume as well as loss of GSIS (Prentki and Nolan, 2006). FKN has been shown to increase survival of microglial cells and vascular smooth muscle cells through a CX3CR1-PI3K-Akt-dependent pathway (Boehme et al., 2000; Chandrasekar et al., 2003). Therefore, whether FKN has in vitro effects on beta cell growth and survival was assessed. As shown in FIG. 16A, FKN prevented beta cell apoptosis induced by chronic palmitate treatment, and this effect was comparable to that observed with GLP1 treatment. Moreover, FKN increased the number of viable cells, which was reduced by chronic palmitate treatment (FIGS. 16B and 16C). Interestingly, the increase in viable cell number by FKN was comparable to the degree of inhibition of beta cell apoptosis, suggesting that the increase of beta cell number was due to reduced apoptosis, rather than increased proliferation. Consistent with this, CX3CR1 KO did not change the number of Ki67 positive proliferating cells on both chow and HFD (FIG. 16D). FKN stimulated Akt phosphorylation, which was inhibited by Wortmannin (FIG. 16E). Moreover, the preventative effect of FKN against palmitate-induced apoptosis was inhibited by Wortmannin (FIG. 16F), suggesting that the anti-apoptotic effect of FKN operates through a PI3K-Akt-dependent mechanism.

Example 7

Islet FKN Expression is Decreased by Aging and HFD

Figure 7A:
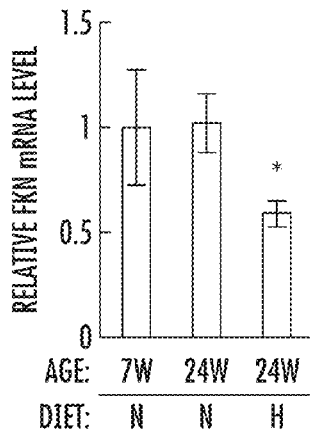
Figure 7B:
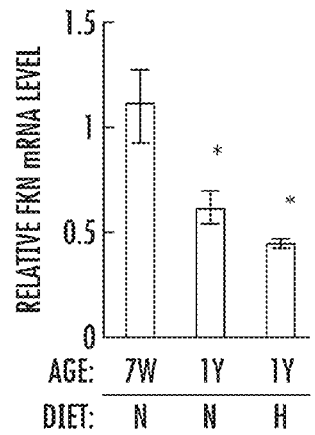
Figure 7C:
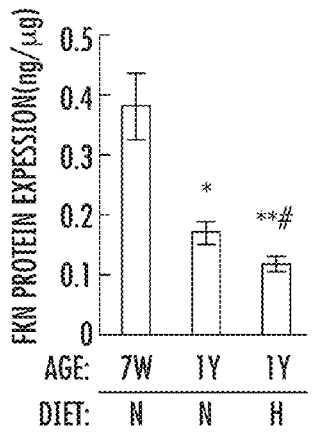
Figures 1, 7D:
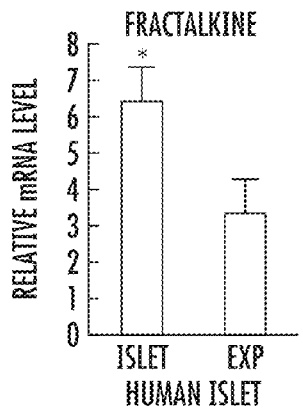
Figures 2, 7D:
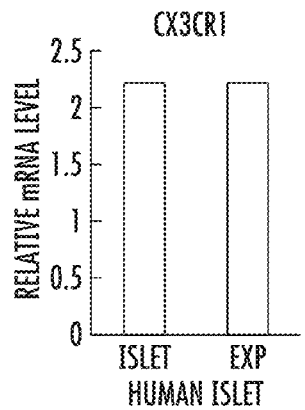
Figure 8:
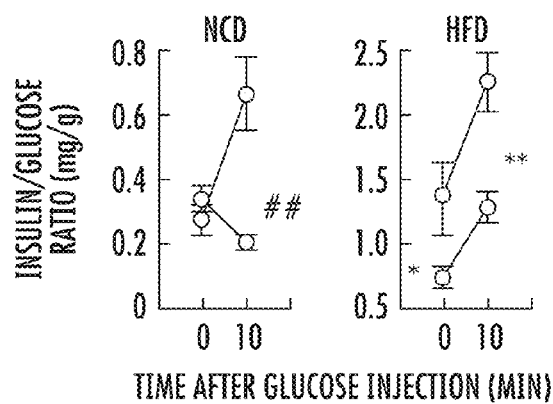

Aging and obesity are major risk factors for beta cell dysfunction. It was found that mRNA and protein levels of FKN were decreased in islets from old or HFD/obese/diabetic mice (FIGS. 7A to 7C). On the other hand, CX3CR1 expression was not affected by aging or HFD (data not shown). Interestingly, FKN expression was not decreased after 24 weeks of age on normal chow, but was significantly decreased in the same age mice by 16 weeks of HFD, suggesting that HFD accelerates the decreased FKN expression in aging. Ex vivo expansion of beta cells causes dedifferentiation and loss of beta cell function. To evaluate whether reduced FKN/CX3CR1 signaling correlates with beta cell differentiation status, FKN and CX3CR1 mRNA levels were compared in human islets and ex vivo expanded human beta cells. As seen in FIGS. 7D-1 to 7D-2, FKN, but not CX3CR1, expression was significantly decreased in expanded human islet-derived cells. It was previously demonstrated that expanded human islet cells dedifferentiate and go through an epithelial to mesenchymal transition in vitro (Kayali et al., 2007; Kutlu et al., 2009), such that the resulting expanded cells are closer in phenotype to mesenchymal stem cells than to the original endocrine cells.

Certainly, beta cell dysfunction in diabetes is a complicated, multi-factorial process, involving factors in addition to FKN/CX3CR1. Several other possibilities also come to mind. First, it is possible that the local expression of soluble FKN is dominant over the circulating levels and that intra-islet FKN levels are low in Type 2 diabetes, similar to what have observed in aging and HFD/obese islets in mice. Secondly, CX3CR1 signaling could be impaired in diabetic beta cells leading to FKN resistance. Finally, while FKN levels are not decreased, it is possible that CX3CR1 expression is decreased in beta cells from Type 2 diabetes patients, although we did not observe this in islets from aging or HFD/obese mice.

REFERENCES

1. Ahren, B., Larsson, H., and Holst, J. J. (1997). Effects of glucagon-like peptide-1 on islet function and insulin sensitivity in noninsulin-dependent diabetes mellitus. The Journal of clinical endocrinology and metabolism 82, 473-478.
2. Aoyama, T., Inokuchi, S., Brenner, D. A., and Seki, E. (2010). CX3CL1-CX3CR1 interaction prevents carbon tetrachloride-induced liver inflammation and fibrosis in mice. Hepatology 52, 1390-1400.
3. Boehme, S. A., Lio, F. M., Maciejewski-Lenoir, D., Bacon, K. B., and Conlon, P. J. (2000). The chemokine fractalkine inhibits Fas-mediated cell death of brain microglia. J Immunol 165, 397-403.
4. Calabrese, A., Zhang, M., Serre-Beinier, V., Caton, D., Mas, C., Satin, L. S., and Meda, P. (2003). Connexin 36 controls synchronization of Ca2+ oscillations and insulin secretion in MIN6 cells. Diabetes 52, 417-424.

5. Cardona, A. E., Pioro, E. P., Sasse, M. E., Kostenko, V., Cardona, S. M., Dijkstra, I. M., Huang, D., Kidd, G., Dombrowski, S., Dutta, R., et al. (2006). Control of microglial neurotoxicity by the fractalkine receptor. Nature neuroscience 9, 917-924.

6. Carvalho, C. P., Barbosa, H. C., Britan, A., Santos-Silva, J. C., Boschero, A. C., Meda, P., and Collares-Buzato, C. B. (2010). Beta cell coupling and connexin expression change during the functional maturation of rat pancreatic islets. Diabetologia 53, 1428-1437.

7. Chandrasekar, B., Mummidi, S., Perla, R. P., Bysani, S., Dulin, N. O., Liu, F., and Melby, P. C. (2003). Fractalkine (CX3CL1) stimulated by nuclear factor kappaB (NF-kappaB)-dependent inflammatory signals induces aortic smooth muscle cell proliferation through an autocrine pathway. The Biochemical journal 373, 547-558.

8. Cho, I. S., Jung, M., Kwon, K. S., Moon, E., Cho, J. H., Yoon, K. H., Kim, J. W., Lee, Y. D., Kim, S. S., and Suh-Kim, H. (2012). Deregulation of CREB Signaling Pathway Induced by Chronic Hyperglycemia Downregulates NeuroD Transcription. PloS one 7, e34860.

9. Combadiere, C., Potteaux, S., Gao, J. L., Esposito, B., Casanova, S., Lee, E. J., Debre, P., Tedgui, A., Murphy, P. M., and Mallat, Z. (2003). Decreased atherosclerotic lesion formation in CX3CR1/apolipoprotein E double knockout mice. Circulation 107, 1009-1016.

10. Defronzo, R. A. (2009). Banting Lecture. From the triumvirate to the ominous octet: a new paradigm for the treatment of type 2 diabetes mellitus. Diabetes 58, 773-795.

11. Eberhard, D., Kragl, M., and Lammert, E. (2010). 'Giving and taking': endothelial and beta-cells in the islets of Langerhans. Trends in endocrinology and metabolism: TEM 21, 457-463.

12. Favre, D., Niederhauser, G., Fahmi, D., Plaisance, V., Brajkovic, S., Beeler, N., Allagnat, F., Haefliger, J. A., Regazzi, R., Waeber, G., et al. (2011). Role for inducible cAMP early repressor in promoting pancreatic beta cell dysfunction evoked by oxidative stress in human and rat islets. Diabetologia 54, 2337-2346.

13. Fong, A. M., Alam, S. M., Imai, T., Haribabu, B., and Patel, D. D. (2002). CX3CR1 tyrosine sulfation enhances fractalkine-induced cell adhesion. The Journal of biological chemistry 277, 19418-19423.

14. Garton, K. J., Gough, P. J., Blobel, C. P., Murphy, G., Greaves, D. R., Dempsey, P. J., and Raines, E. W. (2001). Tumor necrosis factor-alpha-converting enzyme (ADAM17) mediates the cleavage and shedding of fractalkine (CX3CL1). The Journal of biological chemistry 276, 37993-38001.

15. Giordano, E., Cirulli, V., Bosco, D., Rouiller, D., Halban, P., and Meda, P. (1993). B-cell size influences glucose-stimulated insulin secretion. The American journal of physiology 265, C358-364.

16. Guenifi, A., Ahren, B., and Abdel-Halim, S. M. (2001). Differential effects of glucagon-like peptide-1 (7-36) amide versus cholecystokinin on arginine-induced islet hormone release in vivo and in vitro. Pancreas 22, 58-64.

17. Haskell, C. A., Cleary, M. D., and Charo, I. F. (1999). Molecular uncoupling of fractalkine-mediated cell adhesion and signal transduction. Rapid flow arrest of CX3CR1-expressing cells is independent of G-protein activation. The Journal of biological chemistry 274, 10053-10058.

18. Hotamisligil, G. S., Arner, P., Caro, J. F., Atkinson, R. L., and Spiegelman, B. M. (1995). Increased adipose tissue expression of tumor necrosis factor-alpha in human obesity and insulin resistance. The Journal of clinical investigation 95, 2409-2415.

19. Hundhausen, C., Misztela, D., Berkhout, T. A., Broadway, N., Saftig, P., Reiss, K., Hartmann, D., Fahrenholz, F., Postina, R., Matthews, V., et al. (2003). The disintegrin-like metalloproteinase ADAM10 is involved in constitutive cleavage of CX3CL1 (fractalkine) and regulates CX3CL1-mediated cell-cell adhesion. Blood 102, 1186-1195.

20. Hussain, M. A., Daniel, P. B., and Habener, J. F. (2000). Glucagon stimulates expression of the inducible cAMP early repressor and suppresses insulin gene expression in pancreatic beta-cells. Diabetes 49, 1681-1690.

21. Imai, T., Hieshima, K., Haskell, C., Baba, M., Nagira, M., Nishimura, M., Kakizaki, M., Takagi, S., Nomiyama, H., Schall, T. J., et al. (1997). Identification and molecular characterization of fractalkine receptor CX3CR1, which mediates both leukocyte migration and adhesion. Cell 91, 521-530.

22. Jonas, J. C., Sharma, A., Hasenkamp, W., Ilkova, H., Patane, G., Laybutt, R., Bonner-Weir, S., and Weir, G. C. (1999). Chronic hyperglycemia triggers loss of pancreatic beta cell differentiation in an animal model of diabetes. The Journal of biological chemistry 274, 14112-14121.

23. Kayali, A. G., Flores, L. E., Lopez, A. D., Kutlu, B., Baetge, E., Kitamura, R., Hao, E., Beattie, G. M., and Hayek, A. (2007). Limited capacity of human adult islets expanded in vitro to redifferentiate into insulin-producing beta-cells. Diabetes 56, 703-708.

24. Kutlu, B., Kayali, A. G., Jung, S., Parnaud, G., Baxter, D., Glusman, G., Goodman, N., Behie, L. A., Hayek, A., and Hood, L. (2009). Meta-analysis of gene expression in human pancreatic islets after in vitro expansion. Physiological genomics 39, 72-81.

25. Lammert, E., Gu, G., McLaughlin, M., Brown, D., Brekken, R., Murtaugh, L. C., Gerber, H. P., Ferrara, N., and Melton, D. A. (2003). Role of VEGF-A in vascularization of pancreatic islets. Current biology: CB 13, 1070-1074.

26. Lee, Y. S., Choi, J. W., Hwang, I., Lee, J. W., Lee, J. H., Kim, A. Y., Huh, J. Y., Koh, Y. J., Koh, G. Y., Son, H. J., et al. (2010). Adipocytokine orosomucoid integrates inflammatory and metabolic signals to preserve energy homeostasis by resolving immoderate inflammation. The Journal of biological chemistry 285, 22174-22185.

27. Lee, Y. S., Li, P., Huh, J. Y., Hwang, I. J., Lu, M., Kim, J. I., Ham, M., Talukdar, S., Chen, A., Lu, W. J., et al. (2011). Inflammation is necessary for long-term but not short-term high-fat diet-induced insulin resistance. Diabetes 60, 2474-2483.

28. Lesnik, P., Haskell, C. A., and Charo, I. F. (2003). Decreased atherosclerosis in CX3CR1−/− mice reveals a role for fractalkine in atherogenesis. The Journal of clinical investigation 111, 333-340.

29. Lucas, A. D., Chadwick, N., Warren, B. F., Jewell, D. P., Gordon, S., Powrie, F., and Greaves, D. R. (2001). The transmembrane form of the CX3CL1 chemokine fractalkine is expressed predominantly by epithelial cells in vivo. The American journal of pathology 158, 855-866.

30. Maclean, N., and Ogilvie, R. F. (1955). Quantitative estimation of the pancreatic islet tissue in diabetic subjects. Diabetes 4, 367-376.

31. Morris, D. L., Oatmen, K. E., Wang, T., DelProposto, J. L., and Lumeng, C. N. (2012). CX3CR1 deficiency does not influence trafficking of adipose tissue macrophages in mice with diet-induced obesity. Obesity (Silver Spring) 20, 1189-1199.

32. Olefsky, J. M., and Glass, C. K. (2010). Macrophages, inflammation, and insulin resistance. Annual review of physiology 72, 219-246.
33. Pende, M., Kozma, S. C., Jaquet, M., Oorschot, V., Burcelin, R., Le Marchand-Brustel, Y., Klumperman, J., Thorens, B., and Thomas, G. (2000). Hypoinsulinaemia, glucose intolerance and diminished beta-cell size in S6K1-deficient mice. Nature 408, 994-997.
34. Pick, A., Clark, J., Kubstrup, C., Levisetti, M., Pugh, W., Bonner-Weir, S., and Polonsky, K. S. (1998). Role of apoptosis in failure of beta-cell mass compensation for insulin resistance and beta-cell defects in the male Zucker diabetic fatty rat. Diabetes 47, 358-364.
35. Prentki, M., and Nolan, C. J. (2006). Islet beta cell failure in type 2 diabetes. The Journal of clinical investigation 116, 1802-1812.
36. Rahier, J., Guiot, Y., Goebbels, R. M., Sempoux, C., and Henquin, J. C. (2008). Pancreatic beta-cell mass in European subjects with type 2 diabetes. Diabetes, obesity & metabolism 10 *Suppl* 4, 32-42.
37. Seino, S., Shibasaki, T., and Minami, K. (2011). Dynamics of insulin secretion and the clinical implications for obesity and diabetes. The Journal of clinical investigation 121, 2118-2125.
38. Shah, R., Hinkle, C. C., Ferguson, J. F., Mehta, N. N., Li, M., Qu, L., Lu, Y., Putt, M. E., Ahima, R. S., and Reilly, M. P. (2011). Fractalkine is a novel human adipochemokine associated with type 2 diabetes. Diabetes 60, 1512-1518.
39. Sirois-Gagnon, D., Chamberland, A., Perron, S., Brisson, D., Gaudet, D., and Laprise, C. (2011). Association of common polymorphisms in the fractalkine receptor (CX3CR1) with obesity. Obesity (Silver Spring) 19, 222-227.
40. Speier, S., Gjinovci, A., Charollais, A., Meda, P., and Rupnik, M. (2007). Cx36-mediated coupling reduces beta-cell heterogeneity, confines the stimulating glucose concentration range, and affects insulin release kinetics. Diabetes 56, 1078-1086.
41. Sweet, I. R., Cook, D. L., DeJulio, E., Wallen, A. R., Khalil, G., Callis, J., and Reems, J. (2004). Regulation of ATP/ADP in pancreatic islets. Diabetes 53, 401-409.
42. Tacke, F., Alvarez, D., Kaplan, T. J., Jakubzick, C., Spanbroek, R., Llodra, J., Garin, A., Liu, J., Mack, M., van Rooijen, N., et al. (2007). Monocyte subsets differentially employ CCR2, CCR5, and CX3CR1 to accumulate within atherosclerotic plaques. The Journal of clinical investigation 117, 185-194.
43. Teupser, D., Pavlides, S., Tan, M., Gutierrez-Ramos, J. C., Kolbeck, R., and Breslow, J. L. (2004). Major reduction of atherosclerosis in fractalkine (CX3CL1)-deficient mice is at the brachiocephalic artery, not the aortic root. Proceedings of the National Academy of Sciences of the United States of America 101, 17795-17800.
44. Weir, G. C., and Bonner-Weir, S. (2004). Five stages of evolving beta-cell dysfunction during progression to diabetes. Diabetes 53 *Suppl* 3, S16-21.
45. Zernecke, A., Shagdarsuren, E., and Weber, C. (2008). Chemokines in atherosclerosis: an update. Arteriosclerosis, thrombosis, and vascular biology 28, 1897-1908.
46. Zhou, Y. P., Marlen, K., Palma, J. F., Schweitzer, A., Reilly, L., Gregoire, F. M., Xu, G. G., Blume, J. E., and Johnson, J. D. (2003). Overexpression of repressive cAMP response element modulators in high glucose and fatty acid-treated rat islets. A common mechanism for glucose toxicity and lipotoxicity? The Journal of biological chemistry 278, 51316-51323.

What is claimed is:

1. A method for increasing insulin secretion comprising administering to a subject in need thereof an effective amount of a composition comprising an agent that activates fractalkine/CX3C chemokine receptor 1, wherein said agent comprises soluble fractalkine.

* * * * *